US009125899B1

(12) United States Patent
Ness et al.

(10) Patent No.: US 9,125,899 B1
(45) Date of Patent: Sep. 8, 2015

(54) MODULATORS OF GTPASES AND THEIR USE

(75) Inventors: Angela-Wandinger Ness, Albuquerque, NM (US); Laurie Hudson, Albuquerque, NM (US); Larry Sklar, Albuquerque, NM (US); Zurab Surviladze, Albuquerque, NM (US); Tudor Oprea, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 272 days.

(21) Appl. No.: 13/161,766

(22) Filed: Jun. 16, 2011

Related U.S. Application Data

(60) Provisional application No. 61/397,864, filed on Jun. 17, 2010.

(51) Int. Cl.
*A61K 31/403* (2006.01)

(52) U.S. Cl.
CPC .................................... *A61K 31/403* (2013.01)

(58) Field of Classification Search
None
See application file for complete search history.

(56) References Cited

U.S. PATENT DOCUMENTS

| 5,626,838 | A | * | 5/1997 | Cavanaugh, Jr. ................. 424/54 |
| 5,955,504 | A | * | 9/1999 | Wechter et al. ................ 514/568 |
| 6,472,433 | B2 | * | 10/2002 | Wechter ........................ 514/570 |
| 2002/0103141 | A1 | * | 8/2002 | McKearn et al. ................ 514/43 |
| 2006/0183786 | A1 | * | 8/2006 | Wang ............................ 514/412 |

OTHER PUBLICATIONS

Long et al., Treatment of Vinorelbine-Associated Tumor Pain, 2001, Am. J. Clin. Oncol., vol. 24, Issue 4, pp. 414-415.*
Ellenbroek, S. I., and Collard, J. G. (2007) Rho GTPases: functions and association with cancer, Clin Exp Metastasis 24; 657-672.
Bosco, E. E., Mulloy, J. C., and Zheng, Y. (2009) Rac1 GTPase: a "Rac" of all trades, Cell Mol Life Sci 66, 370-374.
Heasman, S. J., and Ridley, A. J. (2008) Mammalian Rho GTPases: new insights into their functions from in vivo studies, Nat Rev Mol Cell Biol 9, 690-701.
Jaffe, A. B., and Hall, A. (2005) Rho GTPases: biochemistry and biology, Annu Rev Cell Dev Biol 21, 247-269.
Karlsson, R., Pedersen, E. D., Wang, Z., and Brakebusch, C. (2009) Rho GTPase function in tumorigenesis, Biochim Biophys Acta 1796, 91-98.
Ridley, A. J. (2006) Rho GTPases and actin dynamics in membrane protrusions and vesicle trafficking, Trends Cell Biol 16, 522-529.
Vega, F. M., and Ridley, A. J. (2008) Rho GTPases in cancer cell biology, FEBS Lett 582, 2093-2101.
Wennerberg, K., Rossman, K. L., and Der, C. J. (2005) The Ras superfamily at a glance, J Cell Sci 118, 843-846.
Fritz, G., and Kaina, B. (2006) Rho GTPases: promising cellular targets for novel anticancer drugs, Curr Cancer Drug Targets 6, 1-14.

Kamai, T., Yamanishi, T., Shirataki, H., Takagi, K., Asami, H., Ito, Y., and Yoshida, K. (2004) Overexpression of RhoA, Rac1, and Cdc42 GTPases is associated with progression in testicular cancer, Clin Cancer Res 10, 4799-4805.
Liu, Y., Wang, Y., Zhang, Y., Miao, Y., Zhao, Y., Zhang, P. X., Jiang, G. Y., Zhang, J. Y., Han, Y., Lin, X. Y., Yang, L. H., Li, Q. C., Zhao, C., and Wang, E. H. (2009) Abnormal expression of p120-catenin, E-cadherin, and small GTPases is significantly associated with malignant phenotype of human lung cancer, Lung Cancer 63, 375-382.
Schnelzer, A., Prechtel, D., Knaus, U., Dehne, K., Gerhard, M., Graeff, H., Harbeck, N., Schmitt, M., and Lengyel, E. (2000) Rac1 in human breast cancer: overexpression, mutation analysis, and characterization of a new isoform, Rac1b, Oncogene 19, 3013-3020.
Sun, D., Xu, D., and Zhang, B. (2006) Rac signaling in tumorigenesis and as target for anticancer drug development, Drug Resist Updat 9, 274-287.
Horiuchi, A., Imai, T., Wang, C., Ohira, S., Feng, Y., Nikaido, T., and Konishi, I. (2003) Up-regulation of small GTPases, RhoA and RhoC, is associated with tumor progression in ovarian carcinoma, Lab Invest 83, 861-870.
Horiuchi, A., Kikuchi, N., Osada, R., Wang, C., Hayashi, A., Nikaido, T., and Konishi, I. (2008) Overexpression of RhoA enhances peritoneal dissemination: RhoA suppression with Lovastatin may be useful for ovarian cancer, Cancer Sci 99, 2532-2539.
Ferri, N., Corsini, A., Bottino, P., Clerici, F., and Contini, A. (2009) Virtual screening approach for the identification of new Rac1 inhibitors, J Med Chem 52, 4087-4090.
Nassar, N., Cancelas, J., Zheng, J., Williams, D. A., and Zheng, Y. (2006) Structure-function based design of small molecule inhibitors targeting Rho family GTPases, Curr Top Med Chem 6, 1109-1116.
Sebti, S. M., and Hamilton, A. D. (2000) Farnesyltransferase and geranylgeranyltransferase I inhibitors in cancer therapy: important mechanistic and bench to bedside issues, Expert Opin Investig Drugs 9, 2767-2782.

(Continued)

*Primary Examiner* — James D Anderson
*Assistant Examiner* — Meghan Finn
(74) *Attorney, Agent, or Firm* — Henry D. Coleman; R. Neil Sudol

(57) ABSTRACT

The present invention relates to molecules which function as modulators (i.e., inhibitors and agonists) of the Ras-homologous (Rho) family of small GTPases (e.g. Rac, Cdc42 and Rho GTPases) and their use to treat diseases, including cancers (including solid tumors-medulloblastoma, ovarian, breast, head and neck, testicular, prostate among others and hematologic malignancies-B cell lymphoma, where these GTPases are overexpressed or hyperactivated), sporadic and genetic diseases where activation of Rho GTPases plays a pivotal role (Menkes disease, rheumatoid arthritis, atherosclerosis, diabetes (type 1), Huntington's disease and Alzheimer's disease) which are mediated through these proteins. Compounds according to the present invention may also be used as a therapy for the treatment of *Entamoeba* spp. or *Acanthamoeba* spp, infections, especially including *Entamoeba histolytica*.

9 Claims, 15 Drawing Sheets

(56) References Cited

OTHER PUBLICATIONS

Surviladze, Z., Waller, A., Wu, Y., Romero, E., Edwards, B. S., Wandinger-Ness, A., and Sklar, L. A. (2010) Identification of a small GTPase inhibitor using a high-throughput flow cytometry bead-based multiplex assay, J Biomol Screen 15, 10-20.

Agola, J. O., Surviladze, Z., Buranda, T., Ursu, O., Hong, L., Waller, A., Strouse, J. J., Simpson, D. S., Schroeder, C. E., Golden, J. E., Oprea, T. I., Sklar, L. A., and Wandinger-Ness, A. (2011) A Competitive Nucleotide Binding Inhibitor: In vitro Characterization of Rab7 GTPase Inhibition, ACS Chemical Biology Submitted.

Carabaza, A., Cabre, F. Rotlian, E., Gomez, M., Gutierrez, M., Garcia, M. L., and Mauleon, D. (1996) Stereoselective inhibition of inducible cyclooxygenase by chiral nonsteroidal antiinflammatory drugs, J Clin Pharmacol 36, 505-512.

Duggan, K. C., Walters, M. J., Musee, J., Harp, J. M., Kiefer, J. R., Oates, J. A., and Marnett, L. J. (2010) Molecular basis for cyclooxygenase inhibition by the non-steroidal anti-inflammatory drug naproxen, J Biol Chem 285, 34950-34959.

Rosenblatt, A. E., Garcia, M. I., Lyons, L., Xie, Y., Maiorino, C., Desire, L., Slingerland, J., and Burnstein, K. L. (2011) Inhibition of the Rho GTPase, Rac1, decreases estrogen receptor levels and is a novel therapeutic strategy in breast cancer, Endocr Relat Cancer 18, 207-219.

Barbolina, M. V., Moss, N. M., Westfall, S. D., Liu, Y., Burkhalter, R. J., Marga, F., Forgacs, G., Hudson, L. G., and Stack, M. S. (2009) Microenvironmental regulation of ovarian cancer metastasis, Cancer Treat Res 149, 319-334.

Dummler, B., Ohshiro, K., Kumar, R., and Field, J. (2009) Pak protein kinases and their role in cancer, Cancer Metastasis Rev 28, 51-63.

Takenawa, T., and Miki, H. (2001) WASP and WAVE family proteins: key molecules for rapid rearrangement of cortical actin filaments and cell movement, J Cell Sci 114, 1801-1809.

White, C. D., Brown, M. D., and Sacks, D. B. (2009) IQGAPs in cancer: a family of scaffold proteins underlying tumorigenesis, FEBS Lett 583, 1817-1824.

Buckley, M. M., and Brogden, R. N. (1990) Ketorolac. A review of its pharmacodynamic and pharmacokinetic properties, and therapeutic potential, Drugs 39, 86-109.

Cohen, A., and Basch, C. (1988) Steady state pharmacokinetics of naproxen in young and elderly healthy volunteers, Semin Arthritis Rheum 17, 7-11.

Furst, D. E., Sarkissian, E., Blocka, K., Cassell, S., Dromgoole, S., Harris, E. R., Hirschberg, J. M., Josephson, N., and Paulus, H. E. (1987) Serum concentrations of salicylate and naproxen during concurrent therapy in patients with rheumatoid arthritis, Arthritis Rheum 30, 1157-1161.

Jung, D., Mroszczak, E., and Bynum, L. (1988) Pharmacokinetics of ketorolac tromethamine in humans after intravenous, intramuscular and oral administration, Eur J Clin Pharmacol 35, 423-425.

Kato, M., Nishida, S., Kitasato, H., Sakata, N., and Kawai, S. (2001) Cyclooxygenase-1 and cyclooxygenase-2 selectivity of non-steroidal anti-inflammatory drugs: investigation using human peripheral monocytes, J Pharm Pharmacol 53, 1679-1685.

Kendall, M. J., Chellingsworth, M. C., Jubb, R., Thawley, A. R., Undre, N. A., and Kill, D. C. (1989) A pharmacokinetic study of the active metabolite of nabumetone in young healthy subjects and older arthritis patients, Eur J Clin Pharmacol 36, 299-305.

Handley, D. A., Cervoni, P., McCray, J. E., and McCullough, J. R. (1998) Preclinical enantioselective pharmacology of (R)- and (S)-ketorolac, J Clin Pharmacol 38, 25S-35S.

Harman, C. A., Turman, M. V., Kozak, K. R., Marnett, L. J., Smith, W. L., and Garavito, R. M. (2007) Structural basis of enantioselective inhibition of cyclooxygenase-1 by S-alpha-substituted indomethacin ethanolamides, J Biol Chem 282, 28096-28105.

Janssen, A., Maier, T. J., Schiffmann, S., Coste, O., Seegel, M., Geisslinger, G., and Grosch, S. (2006) Evidence of COX-2 independent induction of apoptosis and cell cycle block in human colon carcinoma cells after S- or R-ibuprofen treatment, Eur J Pharmacol 540, 24-33.

Jett, M. F., Ramesha, C. S., Brown, C. D., Chiu, S., Emmett, C., Voronin, T., Sun, T., O'Yang, C., Hunter, J. C., Eglen, R. M., and Johnson, R. M. (1999) Characterization of the analgesic and anti-inflammatory activities of ketorolac and its enantiomers in the rat, J Pharmacol Exp Ther 288, 1288-1297.

Kean, W. F., Lock, C. J., Rischke, J., Butt, R., Buchanan, W. W., and Howard-Lock, H. (1989) Effect of R and S enantiomers of naproxen on aggregation and thromboxane production in human platelets, J Pharm Sci 78, 324-327.

Suesa, N., Fernandez, M. F., Gutierrez, M., Rufat, M. J., Rotllan, E., Calvo, L., Mauleon, D., and Carganico, G. (1993) Stereoselective cyclooxygenase inhibition in cellular models by the enantiomers of ketoprofen, Chirality 5, 589-595.

Wechter, W. J. (1994) Drug chirality: on the mechanism of R-aryl propionic acid class NSAIDs. Epimerization in humans and the clinical implications for the use of racemates, J Clin Pharmacol 34, 1036-1042.

Kolluri, S. K., Corr, M., James, S. Y., Bernasconi, M., Lu, D., Liu, W., Cottam, H. B., Leoni, L. M., Carson, D. A., and Zhang, X. K. (2005) The R-enantiomer of the nonsteroidal antiinflammatory drug etodolac binds retinoid X receptor and induces tumor-selective apoptosis, Proc Natl Acad Sci U S A 102, 2525-2530.

Vigil, D., Cherfils, J., Rossman, K. L., and Der, C. J. (2010) Ras superfamily GEFs and GAPs: validated and tractable targets for cancer therapy?, Nat Rev Cancer 10, 842-857.

Desire, L., Bourdin, J., Loiseau, N., Peillon, H., Picard, V., De Oliveira, C., Bachelot, F., Leblond, B., Taverne, T., Beausoleil, E., Lacombe, S., Drouin, D., and Schweighoffer, F. (2005) RAC1 inhibition targets amyloid precursor protein processing by gamma-secretase and decreases Abeta production in vitro and in vivo, J Biol Chem 280, 37516-37525.

Shutes, A., Onesto, C., Picard, V., Leblond, B., Schweighoffer, F., and Der, C. J. (2007) Specificity and mechanism of action of EHT 1864, a novel small molecule inhibitor of Rac family small GTPases, J Biol Chem 282, 35666-35678.

Mroszczak, E. J., Jung, D., Yee, J., Bynum, L., Sevelius, H., and Massey, I. (1990) Ketorolac tromethamine pharmacokinetics and metabolism after intravenous, intramuscular, and oral administration in humans and animals, Pharmacotherapy 10, 33S-39S.

Pallapies, D., Peskar, B. A., Brune, K., and Geisslinger, G. (1994) Effects on platelet functions and pharmacokinetics of azapropazone and ketorolac tromethamine given as single parenteral doses, Br J Clin Pharmacol 37, 335-339.

Patrignani, P., Panara, M. R., Greco, A., Fusco, O., Natoli, C., Iacobelli, S., Cipollone, F., Ganci, A., Creminon, C., Maclouf, J., and et, a. (1994) Biochemical and pharmacological characterization of the cyclooxygenase activity of human blood prostaglandin endoperoxide synthases, J Pharmacol Exp Ther 271, 1705-1712.

Whale, A., Hashim, F. N., Fram, S., Jones, G. E., and Wells, C. M. (2011) Signalling to cancer cell invasion through PAK family kinases, Front Biosci 16, 849-864.

Brown, L. A., Kalloger, S. E., Miller, M. A., Shih, I., McKinney, S. E., Santos, J. L., Swenerton, K., Spellman, P. T., Gray, J., Gilks, C. B., and Huntsman, D. G. (2008) Amplification of 11q13 in ovarian carcinoma, Genes Chromosomes Cancer 47, 481-489.

Urzua, U., Best, L., and Munroe, D. J. (2010) Microarray proteomic analysis discriminates tumorigenic mouse ovarian surface epithelial cells of divergent aggressive potential, Mol Biosyst 6, 2521-2528.

Fernando, H. S., Sanders, A. J., Kynaston, H. G., and Jiang, W. G. (2010) WAVE3 is associated with invasiveness in prostate cancer cells, Urol Oncol 28, 320-327.

Sossey-Alaoui, K., Li, X., and Cowell, J. K. (2007) c-Abl-mediated phosphorylation of WAVE3 is required for lamellipodia formation and cell migration, J Biol Chem 282, 26257-26265.

Sossey-Alaoui, K., Ranalli, T. A., Li, X., Bakin, A. V., and Cowell, J. K. (2005) WAVE3 promotes cell motility and invasion through the regulation of MMP-1, MMP-3, and MMP-9 expression, Exp Cell Res 308, 135-145.

Siu, M. K, Wong, E. S., Chan, H. Y., Kong, D. S., Woo, N. W., Tam, K. F., Ngan, H. Y., Chan, Q. K., Chan, D. C., Chan, K. Y., and Cheung,

(56) References Cited

OTHER PUBLICATIONS

A. N. (2010) Differential expression and phosphorylation of Pak1 and Pak2 in ovarian cancer: effects on prognosis and cell invasion, Int J Cancer 127, 21-31.
Smith, H. O., Arias-Pulido, H., Kuo, D. Y., Howard, T., Qualls, C. R., Lee, S. J., Verschraegen, C. F., Hathaway, H. J., Joste, N. E., and Prossnitz, E. R. (2009) GPR30 predicts poor survival for ovarian cancer, Gynecol Oncol 114, 465-471.
Madore, J., Ren, F., Filali-Mouhim, A., Sanchez, L., Kobel, M., Tonin, P. N., Huntsman, D., Provencher, D. M., and Mes-Masson, A. M. (2010) Characterization of the molecular differences between ovarian endometrioid carcinoma and ovarian serous carcinoma, J Pathol 220, 392-400.
Holm, C., Rayala, S., Jirstrom, K., Stal, O., Kumar, R., and Landberg, G. (2006) Association between Pak1 expression and subcellular localization and tamoxifen resistance in breast cancer patients, J Natl Cancer Inst 98, 671-680.
Aoki, H., Yokoyama, T., Fujiwara, K., Tari, A. M., Sawaya, R., Suki, D., Hess, K. R., Aldape, K. D., Kondo, S., Kumar, R., and Kondo, Y. (2007) Phosphorylated Pak1 level in the cytoplasm correlates with shorter survival time in patients with glioblastoma, Clin Cancer Res 13, 6603-6609.
Espina, V., Edmiston, K. H., Heiby, M., Pierobon, M., Sciro, M., Merritt, B., Banks, S., Deng, J., VanMeter, A. J., Geho, D. H., Pastore, L., Sennesh, J., Petricoin, E. F. r., and Liotta, L. A. (2008) A portrait of tissue phosphoprotein stability in the clinical tissue procurement process, Mol Cell Proteomics 7, 1998-2018.
Dong, P., Nabeshima, K., Nishimura, N., Kawakami, T., Hachisuga, T., Kawarabayashi, T., and Iwasaki, H. (2006) Overexpression and diffuse expression pattern of IQGAP1 at invasion fronts are independent prognostic parameters in ovarian carcinomas, Cancer Lett 243, 120-127.
Walch, A., Seidl, S., Hermannstadter, C., Rauser, S., Deplazes, J., Langer, R., von Weyhern, C. H., Sarbia, M., Busch, R., Feith, M., Gillen, S., Hofler, H., and Luber, B. (2008) Combined analysis of Rac1, IQGAP1, Tiam1 and E-cadherin expression in gastric cancer, Mod Pathol 21, 544-552.
White, C. D., Khurana, H., Gnatenko, D. V., Li, Z., Odze, R. D., Sacks, D. B., and Schmidt, V. A. (2010) IQGAP1 and IQGAP2 are reciprocally altered in hepatocellular carcinoma, BMC Gastroenterol 10. 125.
Bologa, C. G., Revankar, C. M., Young, S. M., Edwards, B. S., Arterburn, J. B., Kiselyov, A. S., Parker, M. A.,. Tkachenko, S. E., Savchuck, N. P., Sklar, L. A., Oprea, T. I., and Prossnitz, E. R. (2006) Virtual and biomolecular screening converge on a selective agonist for GPR30, Nat Chem Biol 2, 207-212.
Ault, A. (1974) An introduction to enzyme kinetics, J Chem Educ 51, 381-386.
Blat, Y. (2010) Non-competitive inhibition by active site binders, Chem Biol Drug Des 75, 535-540.
Fujita, K., Sugiyama, M., Akiyama, Y., Ando, Y., and Sasaki, Y. (2011) The small-molecule tyrosine kinase inhibitor nilotinib is a potent noncompetitive inhibitor of the SN-38 glucuronidation by human UGT1A1, Cancer Chemother Pharmacol 67, 237-241.
Rowlinson, S. W., Kiefer, J. R., Prusakiewicz, J. J., Pawlitz, J. L., Kozak, K. R., Kalgutkar, A. S., Stallings, W. C., Kurumbail, R. G., and Marnett, L. J. (2003) A novel mechanism of cyclooxygenase-2 inhibition involving interactions with Ser-530 and Tyr-385, J Biol Chem 278, 45763-45769.
Takahashi, Y., Hayashi, I., Tominari, Y., Rikimaru, K., Morohashi, Y., Kan, T., Natsugari, H., Fukuyama, T., Tomita, T., and Iwatsubo, T. (2003) Sulindac sulfide is a noncompetitive gamma-secretase inhibitor that preferentially reduces Abeta 42 generation, J Biol Chem 278, 18664-18670.
Schwartz, S. L., Tessema, M., Buranda, T., Pylypenko, O., Rak, A., Simons, P. C., Surviladze, Z., Sklar, L. A., and Wandinger-Ness, A. (2008) Flow cytometry for real-time measurement of guanine nucloetide binding and exchange by Ras-like GTPases, Anal Biochem 381, 258-266.
Tessema, M., Simons, P. C., Cimino, D. F., Sanchez, L., Waller, A., Posner, R. G., Wandinger-Ness, A., Prossnitz, E. R., and Sklar, L. A. (2006) Glutathione-S-transferase-green fluorescent protein fusion protein reveals slow dissociation from high site density beads and measures free GSH, Cytometry A 69, 326-334.
Pallapies, D., Salinger, A., Meyer zum Gottesberge, A., Atkins, D. J., Rohleder, G., Nagyivanyi, P., and Peskar, B. A. (1995) Effects of lysine clonixinate and ketorolac tromethamine on prostanoid release from various rat organs incubated ex vivo, Life Sci 57, 83-89.
Hinz, B., Cheremina, O., Besz, D., Ziotnick, S., and Brune, K. (2008) Impact of naproxen sodium at over-the-counter doses on cyclooxygenase isoforms in human volunteers, Int J Clin Pharmacol Ther 46, 180-186.
Huntjens, D. R., Spalding, D. J., Danhof, M., and Della Pasqua, O. E. (2006) Correlation between in vitro and in vivo concentration-effect relationships of naproxen in rats and healthy volunteers, Br J Pharmacol 148, 396-404.
Kean, W. F., Lock, C. J., and Howard-Lock, H. E. (1991) Chirality in antirheumatic drugs, Lancet 338, 1565-1568.
Mroszczak, E., Combs, D., Chaplin, M., Tsina, I., Tarnowski, T., Rocha, C., Tam, Y., Boyd, A., Young, J., and Depass, L. (1996) Chiral kinetics and dynamics of ketorolac, J Clin Pharmacol 36, 521-539.
Edwards, B. S., Bologa, C., Young, S. M., Balakin, K. V., Prossnitz, E. R., Savchuck, N. P., Sklar, L. A., and Oprea, T. I. (2005) Integration of virtual screening with high-throughput flow cytometry to identify novel small molecule formylpeptide receptor antagonists, Mol Pharmacol 68, 1301-1310.
Edwards, B. S., Young, S. M., Oprea, T. I., Bologa, C. G., Prossnitz, E. R., and Sklar, L. A. (2006) Biomolecular screening of formylpeptide receptor ligands with a sensitive, quantitative, high-throughput flow cytometry platform, Nat Protoc 1, 59-66.
Lloyd, D. G., Golfis, G., Knox, A. J., Fayne, D., Meegan, M. J., and Oprea, T. I. (2006) Oncology exploration: charting cancer medicinal chemistry space, Drug Discov Today 11, 149-159.
Olah, M. M., Bologa, C. G., and Oprea, T. I. (2004) Strategies for compound selection, Curr Drug Discov Technol 1, 211-220.
Oprea, T. I., Allu, T. K., Fara, D. C., Rad, R. F., Ostopovici, L., and Bologa, C. G. (2007) Lead-like, drug-like or "Pub-like": how different are they?, J Comput Aided Mol Des 21, 113-119.
Oprea, T. I., Tropsha, A., Faulon, J. L., and Rintoul, M. D. (2007) Systems chemical biology, Nat Chem Biol 3, 447-450.
Saunders, M. J., Graves, S. W., Sklar, L. A., Oprea, T. I., and Edwards, B. S. (2010) High-throughput multiplex flow cytometry screening for botulinum neurotoxin type a light chain protease inhibitors, Assay Drug Dev Technol 8, 37-46.
Taboureau, O., Nielsen, S. K., Audouze, K., Weinhold, N., Edsgard, D., Roque, F. S., Kouskoumvekaki, I., Bora, A., Curpan, R., Jensen, T. S., Brunak, S., and Oprea, T. I. (2011) ChemProt: a disease chemical biology database, Nucleic Acids Res 39, D367-72.
Winter, S. S., Lovato, D. M., Khawaja, H. M., Edwards, B. S., Steele, I. D., Young, S. M., Oprea, T. I., Sklar, L. A., and Larson, R. S. (2008) High-throughput screening for daunorubicin-mediated drug resistance identifies mometasone furoate as a novel ABCB1-reversal agent, J Biomol Screen 13, 185-193.
Eberth, A., Dvorsky, R., Becker, C. F., Beste, A., Goody, R. S., and Ahmadian, M. R. (2005) Monitoring the real-time kinetics of the hydrolysis reaction of guanine nucleotide-binding proteins, Biol Chem 386, 1105-1114.
Dvorsky, R., Blumenstein, L., Vetter, I. R., and Ahmadian, M. R. (2004) Structural insights into the interaction of ROCKI with the switch regions of RhoA, J Biol Chem 279, 7098-7104.
Hemsath, L., Dvorsky, R., Fiegen, D., Carlier, M. F., and Ahmadian, M. R. (2005) An electrostatic steering mechanism of Cdc42 recognition by Wiskott-Aldrich syndrome proteins, Mol Cell 20, 313-324.
Rose, R., Weyand, M., Lammers, M., Ishizaki, T., Ahmadian, M. R., and Wittinghofer, A. (2005) Structural and mechanistic insights into the interaction between Rho and mammalian Dia, Nature 435, 513-518.
Gao, Y., Dickerson, J. B., Guo, F., Zheng, J., and Zheng, Y. (2004) Rational design and characterization of a Rac GTPase-specific small molecule inhibitor, Proc Natl Acad Sci U S A 101, 7618-7623.

(56) References Cited

OTHER PUBLICATIONS

Benard, V., and Bokoch, G. M. (2002) Assay of Cdc42, Rac, and Rho GTPase activation by affinity methods, Methods Enzymol 345, 349-359.

Crompton, A. M., Foley, L. H., Wood, A., Roscoe, W., Stokoe, D., McCormick, F., Symons, M., and Bollag, G. (2000) Regulation of Tiam1 nucleotide exchange activity by pleckstrin domain binding ligands, J Biol Chem 275, 25751-25759.

Fisher, K. E., Sacharidou, A., Stratman, A. N., Mayo, A. M., Fisher, S. B., Mahan, R. D., Davis, M. J., and Davis, G. E. (2009) MT1-MMP- and Cdc42-dependent signaling co-regulate cell invasion and tunnel formation in 3D collagen matrices, J Cell Sci 122, 4558-4569.

Machesky, L. M. (2008) Lamellipodia and filopodia in metastasis and invasion, FEBS Lett 582, 2102-2111.

Hudson, L. G., Zeineldin, R., Silberberg, M., and Stack, M. S. (2009) Activated epidermal growth factor receptor in ovarian cancer, Cancer Treat Res 149, 203-226.

Arulanandam, R., Vultur, A., Cao, J., Carefoot, E., Elliott, B. E., Truesdell, P. F., Larue, L., Feracci, H., and Raptis, L. (2009) Cadherin-cadherin engagement promotes cell survival via Rac1/Cdc42 and signal transducer and activator of transcription-3, Mol Cancer Res 7, 1310-1327.

Bourguignon, L. Y. (2008) Hyaluronan-mediated CD44 activation of RhoGTPase signaling and cytoskeleton function promotes tumor progression, Semin Cancer Biol 18, 251-259.

Braga, V. M., and Yap, A. S. (2005) The challenges of abundance: epithelial junctions and small GTPase signalling, Curr Opin Cell Biol 17, 466-474.

Kothapalli, D., Flowers, J., Xu, T., Pure, E., and Assoian, R. K. (2008) Differential activation of ERK and Rac mediates the proliferative and anti-proliferative effects of hyaluronan and CD44, J Biol Chem 283, 31823-31829.

Murai, T., Miyazaki, Y., Nishinakamura, H., Sugahara, K. N., Miyauchi, T., Sako, Y., Yanagida, T., and Miyasaka, M. (2004) Engagement of CD44 promotes Rac activation and CD44 cleavage during tumor cell migration, J Biol Chem 279, 4541-4550.

Nelson, W. J. (2008) Regulation of cell-cell adhesion by the cadherin-catenin complex, Biochem Soc Trans 36, 149-155.

Samarin, S., and Nusrat, A. (2009) Regulation of epithelial apical junctional complex by Rho family GTPases, Front Biosci 14, 1129-1142.

Yamada, S., and Nelson, W. J. (2007) Localized zones of Rho and Rac activities drive initiation and expansion of epithelial cell-cell adhesion, J Cell Biol 178, 517-527.

Burleson, K. M., Boente, M. P., Pambuccian, S. E., and Skubitz, A. P. (2006) Disaggregation and invasion of ovarian carcinoma ascites spheroids, J Transl Med 4, 6.

Burleson, K. M., Casey, R. C., Skubitz, K. M., Pambuccian, S. E., Oegema, T. R. J., and Skubitz, A. P. (2004) Ovarian carcinoma ascites spheroids adhere to extracellular matrix components and mesothelial cell monolayers, Gynecol Oncol 93, 170-181.

Shield, K., Ackland, M. L., Ahmed, N., and Rice, G. E. (2009) Multicellular spheroids in ovarian cancer metastases: Biology and pathology, Gynecol Oncol 113, 143-148.

Casey, R. C., Burleson, K. M., Skubitz, K. M., Pambuccian, S. E., Oegema, T. R. J., Ruff, L. E., and Skubitz, A. P. (2001) Beta 1-integrins regulate the formation and adhesion of ovarian carcinoma multicellular spheroids, Am J Pathol 159, 2071-2080.

Casey, R. C., Oegema, T. R. J., Skubitz, K. M., Pambuccian, S. E., Grindle, S. M., and Skubitz, A. P. (2003) Cell membrane glycosylation mediates the adhesion, migration, and invasion of ovarian carcinoma cells, Clin Exp Metastasis 20, 143-152.

Green, S. K., Francia, G., Isidoro, C., and Kerbel, R. S. (2004) Antiadhesive antibodies targeting E-cadherin sensitize multicellular tumor spheroids to chemotherapy in vitro, Mol Cancer Ther 3, 149-159.

L'Esperance, S., Bachvarova, M., Tetu, B., Mes-Masson, A. M., and Bachvarov, D. (2008) Global gene expression analysis of early response to chemotherapy treatment in ovarian cancer spheroids, BMC Genomics 9, 99.

Lessan, K., Aguiar, D. J., Oegema, T., Siebenson, L., and Skubitz, A. P. (1999) CD44 and beta1 integrin mediate ovarian carcinoma cell adhesion to peritoneal mesothelial cells, Am J Pathol 154, 1525-1537.

Li, C. Z., Liu, B., Wen, Z. Q., and Li, H. Y. (2008) Inhibition of CD44 expression by small interfering RNA to suppress the growth and metastasis of ovarian cancer cells in vitro and in vivo, Folia Biol (Praha) 54, 180-186.

Strobel, T., and Cannistra, S. A. (1999) Beta1-integrins partly mediate binding of ovarian cancer cells to peritoneal mesothelium in vitro, Gynecol Oncol 73, 362-367.

Arlt, M. J., Novak-Hofer, I., Gast, D., Gschwend, V., Moldenhauer, G., Grunberg, J., Honer, M., Schubiger, P. A., Altevogt, P., and Kruger, A. (2006) Efficient inhibition of intra-peritoneal tumor growth and dissemination of human ovarian carcinoma cells in nude mice by anti-L1-cell adhesion molecule monoclonal antibody treatment, Cancer Res 66, 936-943.

Huang, S., Robinson, J. B., Deguzman, A., Bucana, C. D., and Fidler, I. J. (2000) Blockade of nuclear factor-kappaB signaling inhibits angiogenesis and tumorigenicity of human ovarian cancer cells by suppressing expression of vascular endothelial growth factor and interleukin 8, Cancer Res 60, 5334-5339.

Lotan, T., Hickson, J., Souris, J., Huo, D., Taylor, J., Li, T., Otto, K., Yamada, S. D., Macleod, K., and Rinker-Schaeffer, C. W. (2008) c-Jun NH2-terminal kinase activating kinase 1/mitogen-activated protein kinase kinase 4- mediated inhibition of SKOV3ip.1 ovarian cancer metastasis involves growth arrest and p21 up-regulation, Cancer Res 68, 2166-2175.

Novak-Hofer, I., Cohrs, S., Grunberg, J., Friedli, A., Schlatter, M. C., Pfeifer, M., Altevogt, P., and Schubiger, P. A. (2008) Antibodies directed against L1-CAM synergize with Genistein in inhibiting growth and survival pathways in SKOV3ip human ovarian cancer cells, Cancer Lett 261, 193-204.

Shaw, T. J., Senterman, M. K., Dawson, K., Crane, C. A., and Vanderhyden, B. C. (2004) Characterization of intraperitoneal, orthotopic, and metastatic xenograft models of human ovarian cancer, Mol Ther 10, 1032-1042.

Metcalf, K. S., Selby, P. J., Trejdosiewicz, L. K., and Southgate, J. (1998) Culture of ascitic ovarian cancer cells as a clinically-relevant ex vivo model for the assessment of biological therapies, Eur J Gynaecol Oncol 19, 113-119.

Hassan, R., Lerner, M. R., Benbrook, D., Lightfoot, S. A., Brackett, D. J., Wang, Q. C., and Pastan, I. (2002) Antitumor activity of SS(dsFv)PE38 and SS1(dsFv)PE38, recombinant antimesothelin immunotoxins against human gynecologic cancers grown in organotypic culture in vitro, Clin Cancer Res 8, 3520-3526.

Cowden Dahl, K. D., Dahl, R., Kruichak, J. N., and Hudson, L. G. (2009) The epidermal growth factor receptor responsive miR-125a represses mesenchymal morphology in ovarian cancer cells, Neoplasia 11, 1208-1215.

Cowden Dahl, K. D., Symowicz, J., Ning, Y., Gutierrez, E., Fishman, D. A., Adley, B. P., Stack, M. S., and Hudson, L. G. (2008) Matrix metalloproteinase 9 is a mediator of epidermal growth factor-dependent e-cadherin loss in ovarian carcinoma cells, Cancer Res 68, 4606-4613.

Cowden Dahl, K. D., Zeineldin, R., and Hudson, L. G. (2007) PEA3 is necessary for optimal epidermal growth factor receptor-stimulated matrix metalloproteinase expression and invasion of ovarian tumor cells, Mol Cancer Res 5, 413-421.

Moss, N. M., Barbolina, M. V., Liu, Y., Sun, L., Munshi, H. G., and Stack, M. S. (2009) Ovarian cancer cell detachment and multicellular aggregate formation are regulated by membrane type 1 matrix metalloproteinase: a potential role in I. p. metastatic dissemination, Cancer Res 69, 7121-7129.

Symowicz, J., Adley, B. P., Gleason, K. J., Johnson, J. J., Ghosh, S., Fishman, D. A., Hudson, L. G., and Stack, M. S. (2007) Engagement of collagen-binding integrins promotes matrix metalloproteinase-9-dependent E-cadherin ectodomain shedding in ovarian carcinoma cells, Cancer Res 67, 2030-2039.

Zeineldin, R., Rosenberg, M., Ortega, D., Buhr, C., Chavez, M. G., Stack, M. S., Kusewitt, D. F., and Hudson, L. G. (2006) Mesenchymal transformation in epithelial ovarian tumor cells expressing epidermal growth factor receptor variant III, Mol Carcinog 45, 851-860.

(56) References Cited

OTHER PUBLICATIONS

Getsios, S., Amargo, E. V., Dusek, R. L., Ishii, K., Sheu, L., Godsel, L. M., and Green, K. J. (2004) Coordinated expression of desmoglein 1 and desmocollin 1 regulates intercellular adhesion, Differentiation 72, 419-433.

Bressenot, A., Marchal, S., Bezdetnaya, L., Garnier, J., Guillemin, F., and Plenat, F. (2009) Assessment of apoptosis by immunohistochemistry to active caspase-3, active caspase-7, or cleaved PARP in monolayer cells and spheroid and subcutaneous xenografts of human carcinoma, J Histochem Cytochem 57, 289-300.

Kenny, H. A., Krausz, T., Yamada, S. D., and Lengyel, E. (2007) Use of a novel 3D culture model to elucidate the role of mesothelial cells, fibroblasts and extra-cellular matrices on adhesion and invasion of ovarian cancer cells to the omentum, Int J Cancer 121, 1463-1472.

Barbolina, M. V., Adley, B. P., Ariztia, E. V., Liu, Y., and Stack, M. S. (2007) Microenvironmental regulation of membrane type 1 matrix metalloproteinase activity in ovarian carcinoma cells via collagen-induced EGR1 expression, J Biol Chem 282, 4924-4931.

Barbolina, M. V., Adley, B. P., Kelly, D. L., Fought, A. J., Scholtens, D. M., Shea, L. D., and Stack, M. S. (2008) Motility-related actinin alpha-4 is associated with advanced and metastatic ovarian carcinoma, Lab Invest 88, 602-614.

Kenny, H. A., Dogan, S., Zillhardt, M., K Mitra, A., Yamada, S. D., Krausz, T., and Lengyel, E. (2009) Organotypic models of metastasis: A three-dimensional culture mimicking the human peritoneum and omentum for the study of the early steps of ovarian cancer metastasis, Cancer Treat Res 149, 335-351.

Efstathiou, J. A., Sampson, D. A., Levine, Z., Rohan, R. M., Zurakowski, D., Folkman, J., D'Amato, R. J., and Rupnick, M. A. (2005) Nonsteroidal antiinflammatory drugs differentially suppress endometriosis in a murine model, Fertil Steril 83, 171-181.

Greene, A. K., Alwayn, I. P., Nose, V., Flynn, E., Sampson, D., Zurakowski, D., Folkman, J., and Puder, M. (2005) Prevention of intra-abdominal adhesions using the antiangiogenic COX-2 inhibitor celecoxib, Ann Surg 242, 140-146.

Kendig, E. L., Schneider, S. N., Clegg, D. J., Genter, M. B., and Shertzer, H. G. (2008) Over-the-counter analgesics normalize blood glucose and body composition in mice fed a high fat diet, Biochem Pharmacol 76, 216-224.

Kumari, B., Kumar, A., and Dhir, A. (2007) Protective effect of non-selective and selective COX-2-inhibitors in acute immobilization stress-induced behavioral and biochemical alterations, Pharmacol Rep 59, 699-707.

Silakova, J. M., Hewett, J. A., and Hewett, S. J. (2004) Naproxen reduces excitotoxic neurodegeneration in vivo with an extended therapeutic window, J Pharmacol Exp Ther 309, 1060-1066.

Metzner, J., Popp, L., Marian, C., Schmidt, R., Manderscheid, C., Renne, C., Fisslthaler, B., Fleming, I., Busse, R., Geisslinger, G., and Niederberger, E. (2007) The effects of COX-2 selective and non-selective NSAIDs on the initiation and progression of atherosclerosis in ApoE-/-mice, J Mol Med 85, 623-633.

Muller, L. U., Schore, R. J., Zheng, Y., Thomas, E. K., Kim, M. O., Cancelas, J. A., Gu, Y., and Williams, D. A. (2008) Rac guanosine triphosphatases represent a potential target in AML, Leukemia 22, 1803-1806.

Shibata, S., Nagase, M., Yoshida, S., Kawarazaki, W., Kurihara, H., Tanaka, H., Miyoshi, J., Takai, Y., and Fujita, T. (2008) Modification of mineralocorticoid receptor function by Rac1 GTPase: implication in proteinuric kidney disease, Nat Med 14, 1370-1376.

Bryan, B. A., and D'Amore, P. A. (2007) What tangled webs they weave: Rho-GTPase control of angiogenesis, Cell Mol Life Sci 64, 2053-2065.

de Souza Pereira, R. (2009) Selective cyclooxygenase-2 (COX-2) inhibitors used for preventing or regressing cancer, Recent Pat Anticancer Drug Discov 4, 157-163.

Fryer, B. H., and Field, J. (2005) Rho, Rac, Pak and angiogenesis: old roles and newly identified responsibilities in endothelial cells, Cancer Lett 229, 13-23.

Fukumura, D., and Jain, R. K. (2007) Tumor microvasculature and microenvironment: targets for anti-angiogenesis and normalization, Microvasc Res 74, 72-84.

Ingber, D. E. (2008) Can cancer be reversed by engineering the tumor microenvironment?, Semin Cancer Biol 18, 356-364.

Mammoto, A., Mammoto, T., and Ingber, D. E. (2008) Rho signaling and mechanical control of vascular development, Curr Opin Hematol 15, 228-234.

Sarkar, F. H., Adsule, S., Li, Y., and Padhye, S. (2007) Back to the future: COX-2 inhibitors for chemoprevention and cancer therapy, Mini Rev Med Chem 7, 599-608.

Ushio-Fukai, M., and Nakamura, Y. (2008) Reactive oxygen species and angiogenesis: NADPH oxidase as target for cancer therapy, Cancer Lett 266, 37-52.

Wang, M. T., Honn, K. V., and Nie, D. (2007) Cyclooxygenases, prostanoids, and tumor progression, Cancer Metastasis Rev 26, 525-534.

Lin, Y. G., Kunnumakkara, A. B., Nair, A., Merritt, W. M., Han, L. Y., Armaiz-Pena, G. N., Kamat, A. A., Spannuth, W. A., Gershenson, D. M., Lutgendorf, S. K., Aggarwal, B. B., and Sood, A. K. (2007) Curcumin inhibits tumor growth and angiogenesis in ovarian carcinoma by targeting the nuclear factor-kappaB pathway, Clin Cancer Res 13, 3423-3430.

Savagner, P., Kusewitt, D. F., Carver, E. A., Magnino, F., Choi, C., Gridley, T., and Hudson, L. G. (2005) Developmental transcription factor slug is required for effective re-epithelialization by adult keratinocytes, J Cell Physiol 202, 858-866.

Symowicz, J., Adley, B. P., Woo, M. M., Auersperg, N., Hudson, L. G., and Stack, M. S. (2005) Cyclooxygenase-2 functions as a downstream mediator of lysophosphatidic acid to promote aggressive behavior in ovarian carcinoma cells, Cancer Res 65, 2234-2242.

Forget, P., Vandenhende, J., Berliere, M., Machiels, J. P., Nussbaum, B., Legrand, C., and De Kock, M. (2010) Do intraoperative analgesics influence breast cancer recurrence after mastectomy? A retrospective analysis, Anesth Analg 110, 1630-1635.

Handley DA, et al. Preclinical Enantioselective Pharmacology of (R)- and (S)- Ketorolac. J Clin Pharmacol, 1998;38:25S-35S.

Duggan, et al. Molecular Basis for Cyclooxygenase Inhibition by the Non-steroidal Anti-inflammatory Drug Naproxen. Journal of Biological Chemistry, 2010;285(45):34950-34959.

Mroszczak E, et al. Chiral Kinetics and Dynamics of Ketorolac. J Clin Pharmacol, 1996;36:521-539.

\* cited by examiner

FIGURE 3
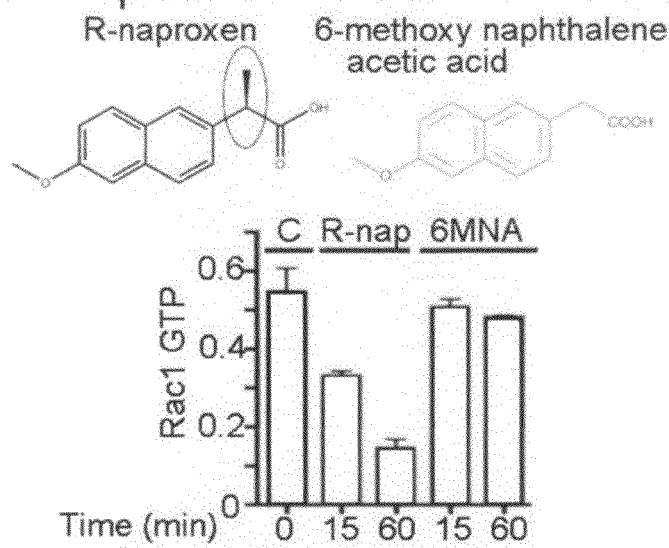
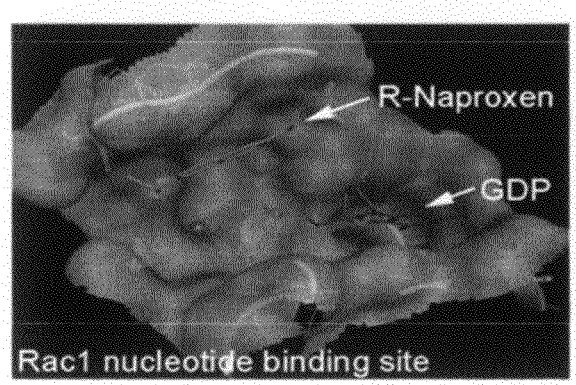

FIGURE 8

TABLE 1

Table 1. Rac1 and Cdc42 effectors to be analyzed

| Pathway(s) | Marker | Activated GTPase | Consequence | Secondary marker |
|---|---|---|---|---|
| Cell Growth, differentiation migration | PAK1 | Rac1 and Cdc42 | PAK phosphorylation, nuclear translocation | pPak, other PAK isoforms |
| Cell-cell adhesion | IQGAP | Rac1 and Cdc42 | IQGAP dissociation from plasma membrane | Nuclear beta-catenin |
| Cell migration, invasion, filopodia | WAVE3 | Cdc42 | Increased WAVE3 expression, altered membrane association | Matrix metallo-proteinases |
| Cell migration, lamellopodia | WASP | Rac1 | Increased WASP expression, altered membrane association | Integrins |

FIGURE 9

TABLE 2

Table 2. Serum concentrations and effective doses of drugs to be tested.

| | S-Nap | R-Nap | 6-MNA | (R,S) Ket | S-Ket | R-Ket | NSC |
|---|---|---|---|---|---|---|---|
| Target | COX 1/2 | Rac1/Cdc42* | COX 1/2 | COX 1>2 | COX 1>2 | Rac1/Cdc42* | Rac1 |
| Serum $C_{max}$ | 413+/-74 µM | NA | 58 µM | 6.4+/-1.8 µM | NA | NA | NA |
| Serum $C_{ave}$ | 130-391 µM | NA | 173-231 µM | 8.3+/-2.3 µM | NA | NA | NA |
| $IC_{50}$COX1 | 35.5-48.3 µM | >100xs-Nap | 149-278 µM | 0.6 µM | 0.1 µM | ND | ND |
| $IC_{50}$COX2 | 64.6-79.5 µM | >100xs-Nap | 187-230 µM | 2.7 µM | 2.5 µM | ND | ND |
| $IC_{50}$Rac1 | >100 µM | TBD | >100 µM | TBD | TBD | TBD | ~50 µM |
| $IC_{50}$(est) migration | ≥300 µM | ~100 µM | >300 µM | 34 µM | >100 µM | 7 µM | <30 µM |

FIGURE 10
GEMFIBROZIL
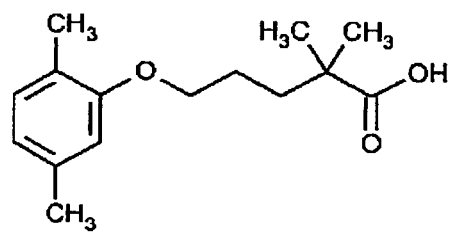
(R)-NAPROXEN
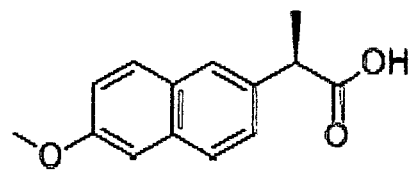
(S) NAPROXEN
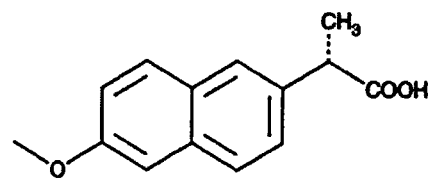

FIGURE 10 (CONT'D)
METHALLENESTRIL
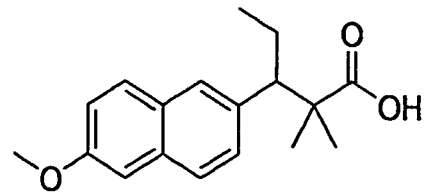
FLUNOXAPROFEN
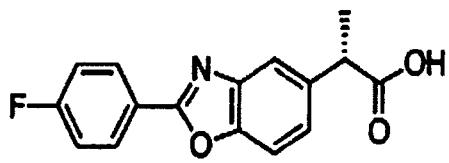
IBUPROFEN
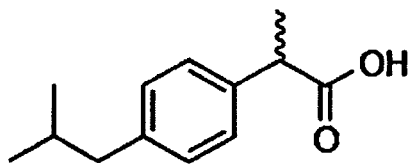
KETOPROFEN
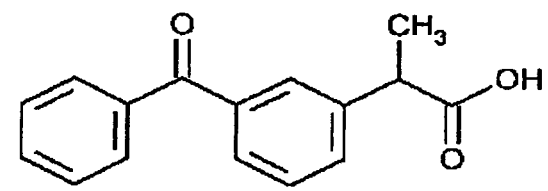

FIGURE 10 (CONT'D)
ECABET
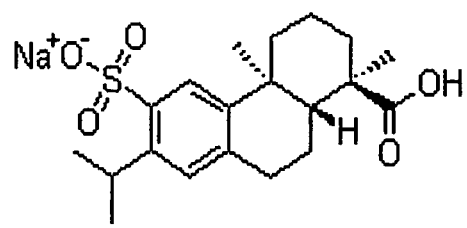
EXATECAN
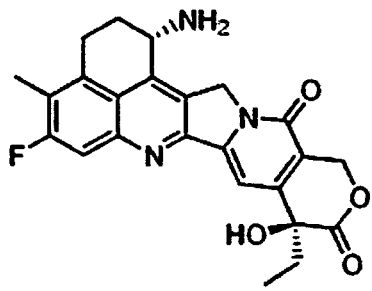
KETORALAC (As Tromethamine Salt)
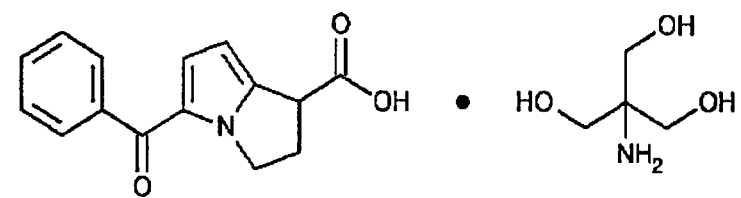

FIGURE 10 (CONT'D)
TANOMASTAT
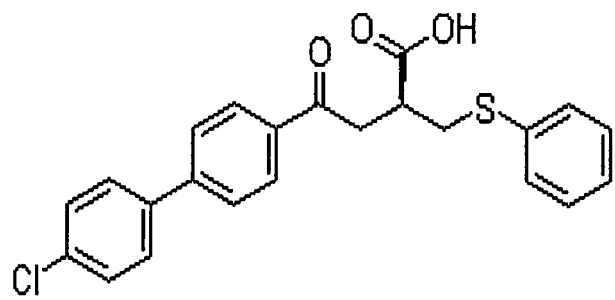
MITIGLINIDE (As Calcium Salt)
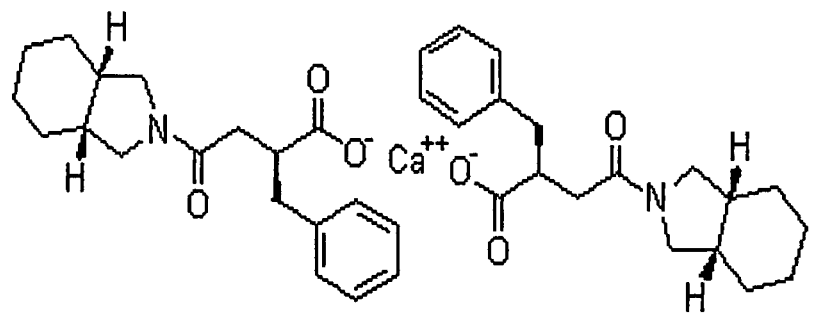
CICLOXILLIC ACID
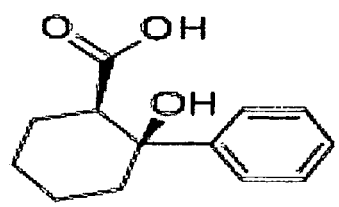

FIGURE 10 (CONT'D)
FEXOFENADINE
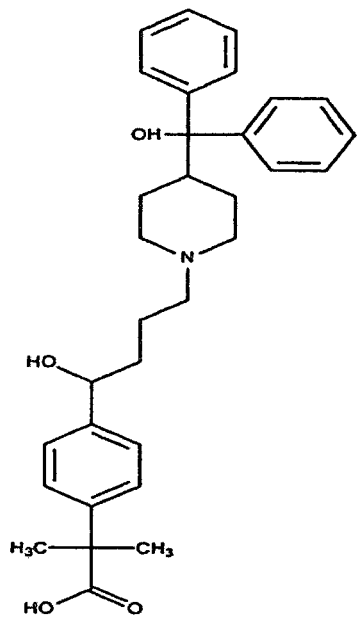
CILOMILAST
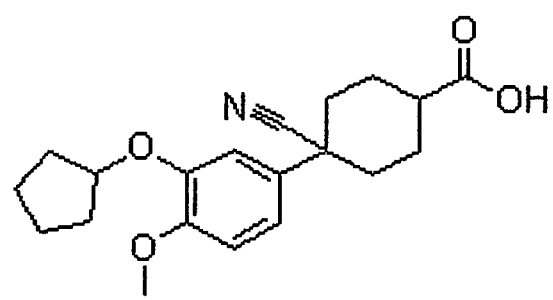

FIGURE 10 (CONT'D)
LEVOCABASTINE
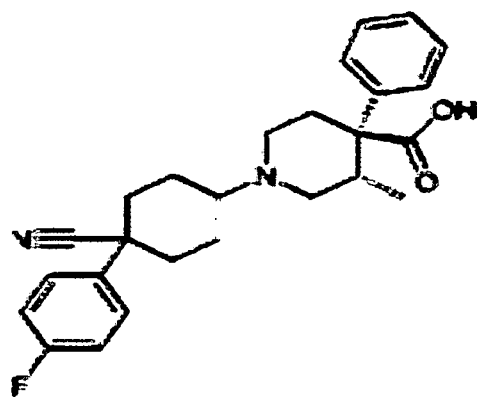
TIAGABINE
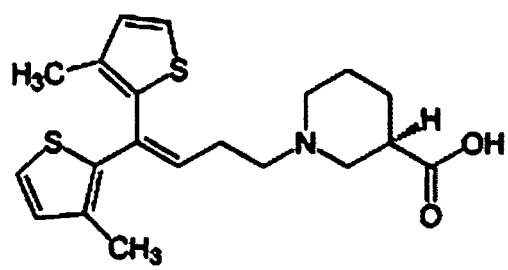
CINALUKAST
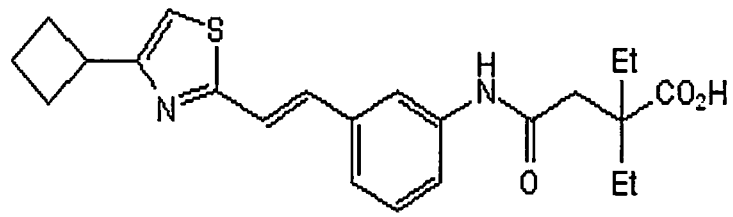

MODULATORS OF GTPASES AND THEIR USE

This invention was made with government support under grants U54MH074425, U54MH084690, R03MH081231 and P30CA118100 awarded by the National Institutes of Health. The government has certain rights in the invention.

FIELD OF THE INVENTION

The present invention relates to molecules which function as modulators (i.e., inhibitors and agonists) of the Ras-homologous (Rho) family of small GTPases (e.g. Rac, Cdc42 and Rho GTPases) and their use to treat diseases, including cancers (including solid tumors-medulloblastoma, ovarian, breast, head and neck, testicular, prostate among others and hematologic malignancies-B cell lymphoma, where these GTPases are overexpressed or hyperactivated), sporadic and genetic diseases where activation of Rho GTPases plays a pivotal role (Menkes disease, rheumatoid arthritis, atherosclerosis, diabetes (type I), Huntington's disease and Alzheimer's disease) which are mediated through these proteins. Compounds according to the present invention may also be used as a therapy for the treatment of *Entamoeba* sp. infections, especially including *Entamoeba histolytica*, as well as other amoeba species responsible for amoebic dysentery as well as other infections, e.g., acanthamoebiasis of the eye caused by *acanthamoeba* spp.

RELATED APPLICATIONS, CLAIM FOR PRIORITY AND GRANT SUPPORT

The present application claims the benefit of priority from provisional application No. 61/397,864, filed Jun. 17, 2010, entitled "Ras-related GTPases as Targets of Non-Steroidal Anti-inflammatory Drugs, which is incorporated by reference in its entirety herein.

BACKGROUND OF THE INVENTION

The Ras-homologous (Rho) family of small GTPases (Rac, Cdc42 and Rho) are key regulators of actin reorganization, cell motility, cell-cell and cell-extracellular matrix (ECM) adhesion as well as of cell cycle progression, gene expression and apoptosis (FIG. 1) [1-8]. In many human cancers (including colon and breast), aberrant Rho-family signaling due to changes in the GTPase itself or in its regulation loops is a critical underpinning of tumor growth and survival, invasion and metastasis [9-13] (FIG. 1). RhoA and RhoC correlate with advanced ovarian cancer and peritoneal dissemination [14; 15]. Although Rac1 and Cdc42 have been recognized as attractive therapeutic targets, specific Rac GTPase inhibitors while effective in culture [16; 17] have not been translated to clinical use and there are no established Cdc42 specific inhibitors. Lovastatin was shown to inhibit Rho GTPase and reduce ovarian metastasis in a xenograft model [15]. However, the use of statins to block GTPase membrane association has met with only modest success due to their broad spectrum inhibition of protein prenylation resulting in pleiotropic effects on many GTPases and pathways [18]. Furthermore, recent animal studies wherein the effects of geranylgeranyltransferase type I deficiency were analyzed revealed an unexpected hyperactivation of Rho GTPases and concomitant severe joint inflammation {Khan, 2011}. Thus, more specific agents for clinical application are urgently needed.

OBJECTS OF THE INVENTION

It is an object of the invention to provide compounds for modulating Rho family GTPases in patients or subjects.

It is another object of the invention to treat disease states and/or conditions which are medicated through targeting of Rho family GTPases.

It is yet another object of the invention to provide pharmaceutical compositions which may be used to modulate, especially inhibit GTPases in patients or subjects.

It is still a further object of the invention to treat cancer, especially ovarian cancer and other cancers where GTPases are overexpressed or hyperactivated utilizing compounds, compostions and/or methods which are presented herein.

It is an additional object of the invention to provide methods for treating sporadic and genetic diseases where activation of Rho GTPases plays a pivotal role including in Menkes disease, rheumatoid arthritis, atherosclerosis, diabetes (type 1), Huntington's disease and Alzheimer's disease.

It still another object of the invention to inhibit and/or an infection of *Acanthamoeba* spp. or *Entamoeba histolytica* or a disease state or condition where *Acanthamoeba* spp. *Entamoeba histolytica* is a causative agent including amoebic dysentery; extraintestinal amoebiasis, amoebic liver abscess; amoeba cutis acanthamoebiasis of the eye; and amoebic lung abscess.

Any one or more of these and/or other objects of the invention may be readily gleaned from a description of the invention which follows.

BRIEF DESCRIPTION OF THE INVENTION

The present invention relates to compounds according to the chemical structure I

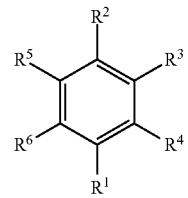

Wherein $R^1$ and $R^2$ are each independently H or a $C_1$-$C_3$ alkyl group;
$R^3$ is a

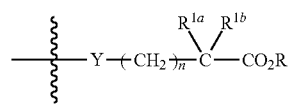

group,
where Y is absent, O or S;
n is 0, 1, 2, 3, 4, 5 or 6;
R is H, a $C_1$-$C_{20}$ alkyl group or a phenyl group optionally substituted with a hydroxyl, halo or $C_1$-$C_3$ alkyl group;
$R^{1a}$ and $R^{1b}$ are each independently H or a $CH_3$ group with the proviso that at least one of $R^{1a}$ and $R^{1b}$ is a methyl group; and
said $$-(CH_2)_n-$$

moiety is optionally substituted with a halo group (F, Cl, Br or I), a $C_1$-$C_3$ alkyl group or a hydroxyl group (preferably, the methylene group alpha to the carbon group containing the $R^{1a}$ and $R^{1b}$ substituents is substituted with a methyl or ethyl group);

$R^4$ is H or a $C_1$ to $C_4$ alkyl group;

$R^5$ is H, halo (F, Cl, Br or I), a $C_1$-$C_6$ linear or branch-chained alkyl group (preferably a $C_1$-$C_4$ alkyl group), a $C_1$-$C_6$ alkoxy group or a

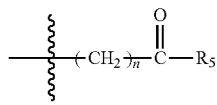

group where $R_5$ is an optionally substituted phenyl or a 5- or 6-membered heteroaryl group, or $R^5$, together with $R^6$, forms an optionally substituted phenyl group (preferably a $C_1$-$C_4$ alkoxy, e.g. methoxy or ethoxy substituted phenyl group) or an optionally substituted 5- or 6-membered heteroaryl ring (preferably, an oxazole ring, preferably substituted with a ortho- or para-halogen e.g. F, Cl, substituted phenyl group) thus forming a bicyclic ring system; and $R^6$ is H, halo, $C_1$-$C_6$ linear or branch-chained alkyl group (preferably, a $C_1$-$C_4$ alkyl group), a $C_1$-$C_6$ alkoxy group or a

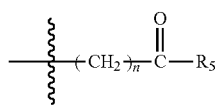

group where $R_5$ is an optionally substituted phenyl or a 5- or 6-membered heteroaryl group, or $R^6$, together with $R^5$, forms an optionally substituted phenyl group or an optionally substituted 5- or 6-membered heteroaryl ring, thus forming an optionally substituted bicyclic ring system, or a pharmaceutically acceptable salt, enantiomer, solvate or polymorph thereof.

In preferred aspects of the invention, $R^5$ and $R^6$ together form a phenyl group which is optionally substituted by at least one methoxy group (preferably, furthermost from the $R^3$ substituent as in naproxen, methallenestril and flunoxaprofen—see FIG. 10 hereof) and $R^4$ is H. In other aspects of the invention, $R^{1a}$ is methyl and $R^{1b}$ is hydrogen providing a chiral center and the possibility of racemic mixtures and individual enantiomers, each of which may be used in the present invention. In substituent $R^3$, n is preferably 0 or 1 and Y is absent. In alternative preferred embodiments, when $R^5$ and $R^6$ together form a phenyl or heteroaryl group, in the $R^3$ substitutent, Y is absent and n is 0 or 1 and when n is 1, the methylene group is substituted with a $C_1$-$C_3$ alkyl (preferably ethyl) and $R^{1a}$ and $R^{1b}$ are both methyl. When n is 0, only one of $R_{1a}$ and $R_{1b}$ is H, thus forming a chiral center. In alternative aspects of the invention where $R^5$ and $R^6$ do not form a ring to create a bicyclic group, Y in $R^3$ is preferably 0 or absent, n is 0, 1, 2, 3, or 4 (preferably 0 or 3), $R^{1a}$ is methyl and $R^{1b}$ is H (thus forming a chiral center). In these monocyclic embodiments, $R^5$ is H or a halogen group, preferably H, $R^6$ is H or a $C_1$-$C_6$ alkyl group (preferably H or a $C_3$ or $C_4$ linear or branch-chained alkyl group, $R^4$ is preferably H and $R^1$ and $R^2$ are H or $CH_3$, preferably H.

The present invention also relates to specific compounds which may be used to modulate GTPases. These compounds include, for example, R-Naproxen, S-Naproxen, methallenestril, R-Flunoxaprofen, S-flunoxaprofen, R-Ibuprofen, S-Ibuprofen, S-Ketoprofen, R-Ketoprofen, gemfibrozil, ecabet, exetecan acid, R-Ketoralac, S-Ketoralac, tanomastat, mitiglinide, cicloxillic acid, fexofenadine, cilomilast, levocabastine, tiagabine, cinalukrast and mixtures thereof, including pharmaceutically acceptable salts, enantiomers, racemic mixtures, solvates and polymorphs thereof. A number of these compounds or their salts is presented in attached FIG. 10.

The compounds which are disclosed herein find use to treat cancers, including solid and epithelial tumors exemplified in this disclosure by ovarian cancer, among others, sporadic or genetic diseases related to hyperactivated membrane trafficking where Rho GTPases are important (e.g. Menkes disease, rheumatoid arthritis, atherosclerosis, diabetes (type I), Huntington's disease and Alzheimer's disease Huntington's), as well as to inhibit *entamoeba histolytica* and/or to treat infections caused by *entamoeba histolytica* as well as other disease states or conditions of *acanthamoeba* spp., such as acanthamoebiasis of the eye.

Accordingly, the present invention relates to a method for modulating, including inhibiting a GTPase in a patient or subject in need of modulation wherein the GTPase is, in particular, a Rac (e.g. Rac1-3) GTPase or Cdc42, the method comprising administering to said patient or subject an effective amount of a compound as set forth hereinabove. The modulator is preferably an antagonist of GTPase. The present invention also relates to methods for modulating disease and/or conditions which are mediated through GTPases, including treating and/or inhibiting the progression of neurologic and inflammatory diseases dependent on Rho GTPases such as Menkes disease, rheumatoid arthritis, atherosclerosis, diabetes (type I), Huntington's disease and Alzheimer's disease; the growth of cancer, including inhibiting and/or reducing the likelihood of the metastasis of cancer comprising administering to a patient or subject in need thereof an effective amount of at least one compound as otherwise disclosed herein. In the case of cancer, compounds according to the present invention may be coadministered with at least one additional anticancer agent to inhibit the growth of and/or otherwise treat the cancer, including reducing the likelihood of metastasis of the treated cancer.

Further embodiments relate to infectious disease, embodied as a method for inhibiting *Entamoeba histolytica* or *Acanthamoeba* spp. and/or treating and/or reducing the likelihood of a disease state or condition in which *Entamoeba histolytica* or *Acanthamoeba* spp. is an infective agent, said method comprising administering to a patient in need of an effective amount of a GTPase inhibitor compound as described herein. Disease states and/or conditions in which *Entamoeba histolytica* is an infective agent include, for example, amoebic dysentery; extraintestinal amoebiasis, amoebic liver abscess; amoeba cutis; and amoebic lung abscess. Disease states or conditions in which *Acanthamoeba* spp. is an infective agent include acanthamoebiasis of the eye (amoeba cutis acanthamoebiasis of the eye), among others.

BRIEF DESCRIPTION OF THE FIGURES

FIG. 3 shows enantiomer selective inhibition of GTPases. (A) GLISA measures cellular effects of small molecules on Rac1. Cells were untreated or incubated with the indicated compound (R-Nap=R-naproxen, enantiomers differ based on orientation of circled methyl group; 6MNA-6-methoxy-2-naphthalene acetic acid) for the indicated times then treated+/−10 ng/ml EGF for 2 min. Equal cell lysate protein was assayed for activated Rac1 using a commercial, plate based Pak-binding assay according to manufacturer's instructions (GLISA, Cytoskeleton, Inc.). Similar results were obtained for Cdc42 and 5-naproxen was inactive (not shown) (B) Docking predicts R-enantiomer-selective binding of naproxen to GDP-bound Rac1. R-naproxen predicted to bind GDP-bound Rac1, but not GTP-bound conformation. S-naproxen is sterically blocked from binding (not shown). Rac1 crystal structure used to dock molecules via FRED (OpenEye).

FIG. 8, Table 1, shows four downstream effectors with keys roles in tumor growth and metastasis. These downstream pathways would be expected to be at least partially inactivated by GTPase inhibition and can be used to monitor compound efficacy.

FIG. 9, Table 2, evidences that the doses effective for GTPase inhibition are doses that are within the dose ranges which are acceptable for human treatment based on COX inhibition). Table 2 shows serum concentrations and effective doses of drugs. Serum concentrations (maximum ($C_{max}$) and steady state ($C_{ave}$)) are based on typical oral dosing (S-Naproxen 500 mg; R,S-ketorolac 30 mg; 6-MNA 1000 mg of nabumetone) and derived from FDA product literature and primary literature (S-Naproxen, [40; 41]; ketorolac [23; 26; 39; 45; 46]; 6-MNA [43; 44; 47]. Note that an IV dose of 30 mg ketorolac achieves a $C_{max}$ of 13.7 µM [46; 71]. $IC_{50}$ values for COX1/2 in human cells were obtained from the literature (R and S-naproxen, [27; 72-74]; R and S-Ketorolac, [23; 26; 39; 46; 71; 75]; 6-MNA, [43; 44; 47], NSC23766, [89]. Migration $IC_{50}$ values were estimated from limited dose response data (FIG. 4) or calculated by GraphPad Prism5 (ketorolac). NA—not applicable, no human dosing; ND=not detected, no COX inhibition; TBD=to be determined.

FIG. 10 sets forth a number of conventional preferred bioactive compounds which may be used in the present invention.

DETAILED DESCRIPTION OF THE INVENTION

Figure 1:
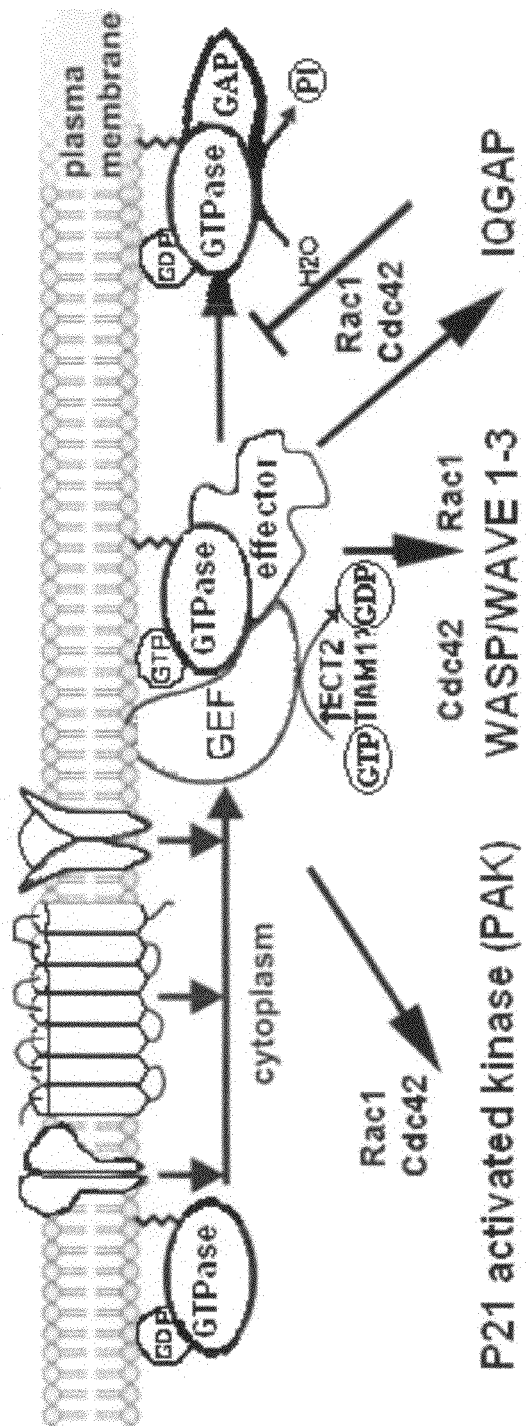
FIG. 1 shows Rac1 and Cdc42 GTPases integrate signaling pathways that are important in cancer growth and metastasis. Activation of tyrosine kinase receptors, G-protein coupled receptors (GPCRs) and integrins causes Rac and Cdc42 GTPases to bind GTP and membranes. The GTP-bound proteins interact with specific downstream effectors to promote actin reorganization that affect changes in cell motility, adhesion, cell growth, gene expression and apoptosis. GTPase functions in the regulation of proliferation, angiogenesis and metastasis are intimately linked to cancer development and progression. Adapted from [1].

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal (i.e., not a laboratory test animal) and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers, individual optical isomers or racemic mixtures, pharmaceutically acceptable salts and prodrug forms. Within its use in context, the term compound may refer to a single compound or a mixture of compounds as otherwise described herein.

The term "bioactive agent" refers to any biologically active compound or drug which may be formulated for use in the present invention. Exemplary bioactive agents include the compounds according to the present invention which are used to modulate GTPases and to treat cancer, other disease states and/or conditions as well as infections caused by *Entamoeba* sp. or *Acanthamoeba* spp. as well as other compounds or agent which are otherwise described herein.

The terms "treat", "treating", and "treatment", are used synonyumously to refer to any action providing a benefit to a patient at risk for or afflicted with a disease, including improvement in the condition through lessening or suppression of at least one symptom, delay in progression of the disease, prevention or delay in the onset of the disease, etc.

Treatment, as used herein, encompasses both prophylactic and therapeutic treatment. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease that subsequently occurs. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate an *Entamoeba* or *Acanthamoeba* infection as otherwise described herein; in another embodiment, administration of the compounds according to the present invention is effective to decrease the severity of the disease or lengthen the lifespan of the mammal so afflicted, in the case of cancer, as well as sporadic and genetic diseases that are Rho GTPase driven, including for example, Menkes disease, rheumatoid arthritis, atherosclerosis, diabetes, Huntington's disease and Alzheimer's disease, among others.

The term "pharmaceutically acceptable" as used herein means that the compound or composition is suitable for administration to a subject to achieve the treatments described herein, without unduly deleterious side effects in light of the severity of the disease and necessity of the treatment.

The term "inhibit" as used herein refers to the partial or complete elimination of a potential effect, while inhibitors are compounds that have the ability to inhibit.

The term "prevention" when used in context shall mean "reducing the likelihood" or preventing a condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients of subjects, administration with compounds according to the present invention will reduce the likelihood or inhibit a particular condition or disease state (in particular, the worsening of a disease state such as the metastasis of cancer or other accepted indicators of disease progression in the case of inflammatory and neurologic diseases) from occurring.

The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. The term cancer also within context, includes drug resistant cancers, including multiple drug resistant cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell lung cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, among others. It is noted that certain epithelial tumors including ovarian, breast, colon, head and neck, medulloblastoma and B-cell lymphoma, among others have all been shown to exhibit increased Rac and Cdc42 expression or activation and are principal target cancers for compounds and therapies according to the present invention.

The term "additional anti-cancer agent" is used to describe an additional compound which may be coadministered with one or more compounds of the present invention in the treatment of cancer. Such agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAKISTAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumurnab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(But)6, Azgly 10] (pyro-Glu-His-Trp-Ser-Tyr-D-Ser(But)-Leu-Arg-Pro-Azgly-NH$_2$acetate[C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, port mer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

The term "alkyl" is used herein to refer to a fully saturated monovalent radical containing carbon and hydrogen (up to 20 carbon atoms as otherwise indicated), and which may be a straight chain, branched or cyclic. Examples of alkyl groups are methyl, ethyl, n-butyl, n-heptyl, isopropyl, 2-methyl propyl, tert-butyl, neopentyl, etc.

The term "substituted" as that term relates to alkyl groups which are described above include one or more functional groups such as lower alkyl groups containing 1-6 carbon atoms, aryl (phenyl or naphthyl), substituted aryl (as described below), acyl ($C_1$-$C_6$), halogen (F, Cl, Br, I, e.g., alkyl halos, e.g., $CF_3$), amido, thioamido, cyano, nitro, alkynyl ($C_2$-$C_6$), azido, hydroxy, alkoxy ($C_1$-$C_6$), amino, $C_1$-$C_6$ alkyl and dialkyl-amino, $C_2$-$C_6$ acylamino, $C_2$-$C_6$ oxyester or carboxyester, aryloxy, aryloxy($C_1$-$C_6$)alkyl, carboxamido, thio, $C_2$-$C_6$ ether or thioether and the like.

The term "aryl", when used in context, refers to a substituted or unsubstituted monovalent aromatic radical having a single ring (e.g., phenyl) or multiple condensed rings (e.g., naphthyl). Other examples include heterocyclic aromatic (heteroaromatic or heteroaryl) ring groups having one or more nitrogen, oxygen, or sulfur atoms in the ring, such as the 5 or 6-membered heteroaryls oxazolyl, isoxazolyl, pyrazolyl, thiazolyl, thiadiazolyl, triazolyl, tetrazolyl, imidazolyl, furyl, pyrrolyl, pyridyl, thienyl, pyridazinyl, pyrimidyl, or the condensed phenyl/heteroaryl ring as otherwise described herein including, for example, benzofuryl, benzothienyl, benzimidazolyl, benzotriazolyl, benzoxazolyl, benzothiazolyl, quinolyl, isoquinolyl and indolyl.

The term "substituted" as used in the term "substituted aryl, substituted aromatic, substituted heteroaryl, or substituted heteroaromatic" herein signifies that one or more substituents (1, 2, 3 or 4, preferably 1 or 2) may be present, said substituents being selected from atoms and groups, which when present do not prevent the compound from functioning as a modulator of GRPase. Examples of substituents that may be present in a substituted aromatic or heteroaromatic group include, but are not limited to, groups such as ($C_1$-$C_6$) alkyl, ($C_1$-$C_{10}$), preferably, ($C_2$-$C_6$) acyl, aryl, heteroaryl, substituted aryl and heteroaryl, halogen, cyano, nitro, amido (optionally substituted with one or two $C_1$-$C_6$ alkyl groups), thioamido (optionally substituted with one or two $C_1$-$C_6$ alkyl groups), azido, alkynyl ($C_2$-$C_6$), ($C_1$-$C_6$) alkylhalos (e.g., $CF_3$), hydroxy, ($C_1$-$C_6$) alkoxy, ($C_2$-$C_8$) alkoxyalkyl, amino, ($C_1$-$C_6$) alkyl and dialkyl amino, ($C_1$-$C_6$ acylamino, ($C_1$-$C_6$) acyloxy, aryloxy, ($C_1$-$C_6$) aryloxyalkyl, ($C_1$-$C_6$) carboxyalkyl, carboxamido, thio, ($C_1$-$C_6$) thioethers, both saturated and unsaturated ($C_3$-$C_8$) cyclic hydrocarbons, ($C_3$-$C_8$) heterocycles and the like. It is noted that each of the substituents disclosed herein may themselves be substituted.

The term "heteroaryl" refers to an unsaturated carbocylic ring wherein one or more carbon atoms have been replaced with one or more heteroatoms such as nitrogen, oxygen or sulfur. Examples of heteroaryls is described above. "5-membered heteroaryl" refers to heteroaryls containing 5 atoms within the heteroaryl ring. "6-ring heteroaryls" refers to heteroaryls containing 6 atoms within the heteroaryl ring. Heteroaryls may be unsubstituted or substituted as otherwise described herein. The term "heterocyclic" refers to a ring system containing from 3 to 8 atoms from 1 to 4 of which are nitrogen, oxygen, or sulfur. 5- or 6-membered heterocycles, when used, are preferred. Heterocycles may be saturated or unsaturated, depending upon the context of use. When unsaturated heterocycles are also referred to as heteroaryls, when fully saturated, they are referred to as heterocycles.

The term "GTPase" is used to describe the Rho family of GTPases, which is a family of small signaling GTPases, of which Rac1, Cdc42 and RhoA are the most well studied members. These GTPases have been shown to regulate many aspects of intracellular dynamics, and play a role in cell proliferation, apoptosis, gene expression, and multiple other common cellular functions. They consequently have utility in the treatment of sporadic and genetic diseases, as well as cancers as described herein. Rac1 is a GTPase regulator of a number of cellular processes, including the cell cycle, cell-cell adhesion, motility (through the actin network), and of epithelial differentiation (for maintaining epidermal stem cells). Cdc42 is a GTPase protein involved in regulation of the cell cycle, cell differentiation and cell migration. RhoA is a GTPase protein which is involved in the regulation and timing of cell division. Together, these GTPase proteins are intimate to processes which are related to cancer and its elaboration and are targets for cancer treatment through modulation, in more particular aspects, inhibition of these GTPase targets. GTPase mediates a number of disease states, including cancer, as otherwise disclosed herein, as well as a number of sporadic and genetic diseases including, for example, Menkes disease, rheumatoid arthritis, atherosclerosis, diabetes (type I), Huntington's disease and Alzheimer's disease, among others.

The term "*Entamoeba*" is used to describe a genus of protozoal anaerobic parasites found as internal parasites or commensals of animals. *Entamoeba histolytica* is an anaerobic parasitic protozoan, part of the genus *Entamoeba* found in humans and responsible for diseases and/or conditions such as Amoebiasis; Amoebic dysentery; Extraintestinal Amoebiasis, Amoebic Liver Abscess; Amoeba Cutis; and Amoebic Lung Abscess ("liver-colored sputum"). *E. histolytica* predominantly infects humans and other primates, as does *E. dispar*, although *E. dispar* is non-pathogenic. Mammals such as dogs and cats can become infected transiently, but are not thought to contribute significantly to transmission. "Additional anti-*entamoeba* agents" are agents which may be combined with those of the present invention and used to inhibit and or/treat *E. histolytica* infections, disease states and/or conditions. These compounds include, for example, metronidazole, bismuth subsalicylate, kaolin pectin, diphenoxyolate, loperamide, quinolones, erythromycin, trimethoprim-sulamethoxazole, ceftriaxine, ampicillin, tetracycline, doxycycline, vancomycin iodoquinol and mixtures thereof. "*Acanthamoeba* spp. is used to describe another genus of protozoal anaerobic parasites found as parasites or commensals of animals, including humans and is responsible for acanthamoebiasis of the eye (amoeba cutis acanthamoebiasis of the eye), which is also treated by compounds according to the present invention.

The term "co-administration" or "adjunct therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time. The term co-administration or adjunct therapy also contemplates other bioactive agents being coadministered with pharmaceutical compositions according to the present invention, especially where a cancer has metastasized or is at risk for metastasis.

Compounds according to the present invention may be readily formulated into pharmaceutical compositions, useful in the treatment of sporadic or genetic diseases or conditions, cancers or infections or conditions caused by *Entamoeba histolytica* or *Acanthamoieba* spp. as described hereinabove. Pharmaceutical compositions comprise an effective amount of one or more compounds according to the present invention in combination with a pharmaceutically acceptable carrier, additive or excipient, optionally in combination with at least one additional anticancer agent.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

As noted above, the compounds and method of the invention modulate GTPase as otherwise described herein, and are useful for the inhibition (including prophylaxis) and/or treatment of cancer, sporadic or genetic diseases or conditions and infections caused by *Entamoeba* sp., including *E. histolytica*, and other amoeba species responsible for amoebic dysentery as well as other infections, e.g., acanthamoebiasis of the eye which is caused by *Acanthamoeba*.

In methods according to the present invention, subjects or patients in need are treated with the present compounds, pharmaceutical compositions in order to inhibit, reduce the likelihood or treat a disease state, condition and/or infection as otherwise described herein. The disease states, conditions and infections treated by the present compounds and compositions are readily recognized and diagnosed by those of ordinary skill in the art and treated by administering to the patient an effective amount of one or more compounds according to the present invention.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to grain quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or are apparent to those skilled in the art; for example, see *Remington's Pharmaceutical Sciences* (17th Ed., Mack Pub. Co., 1985). The composition to be administered will contain a quantity of the selected compound in a pharmaceutically effective amount for modulating GTPase in a subject according to the present invention in a subject.

Synthesis of Compounds According to the Present Invention

The compounds according to the present invention are readily known in the art and their synthesis is well-known and readily provided. Most of the compounds are known in the art and can be found in published literature, purchased from commercial sources or readily prepared from starting materials which are readily obtained from commercial sources. Substituted phenyl or naphthyl compounds, principally used in the present invention are well known in the art. The various substituents may be readily introduced into the pharmacophore, whether that pharmacophore is a phenyl group to which substituents as otherwise presented herein are introduced, a naphthyl group as otherwise described herein or a fused bicyclic benzoheteroaryl group as described herein. Synthesis of all of the presently described compounds are well within the routineer's skill in the art.

Method of Treatment

According to one aspect of the invention, a method is provided for treating a mammalian patient or subject to modulate GTPase, in particular the Rho family of GTPases including Rac (e.g. Rac1), Cdc42 and Rho (e.g. Rho1). Agonist and/or antagonist activity of compounds according to the present invention described herein may be used to modulate GTPase in a manner consistent with inhibiting and/or treating disease states and/or conditions including cancer, sporadic or genetic diseases including Menkes disease, rheumatoid arthritis, atherosclerosis, diabetes (type I), Huntington's disease and Alzheimer's disease, as otherwise described herein and infections caused by *Entamoeba histolytica* or *Acan-* thamoeba spp. Antagonist activity associated with GTPase inhibition is a particularly useful aspect of the present invention.

According to the present invention, in patients or subjects in need thereof, are treated by administering to the patient or subject an effective amount of one or more compounds according to the present invention, optionally in combination with at least one additional bioactive agent useful for treating the same disease state or condition. Compounds according to the present invention may be used to inhibit, reduce the likelihood or treat cancer, including the metastasis of cancer in a patient or subject in need of such treatment. The treatment is useful for any cancer which is mediated by GTPase or for which metastasis is a risk element. Therapy with at least one additional anticancer agent as otherwise described herein is also contemplated in the present methods. The numerous cancers which may be treated pursuant to the present method is described hereinabove.

In another aspect the present invention is directed to a method for treating a sporadic or genetic disease in which activation of Rho GTPase plays a significant role. These disease states and/or conditions include, for example Menkes disease, rheumatoid arthritis, atherosclerosis, diabetes (type I), Huntington's disease and Alzheimer's disease. In this method, a patient or subject in need of treatment is administered an effective amount of a compound as otherwise described herein optionally in combination with a pharmaceutically acceptable carrier, additive or excipient.

In another aspect, the invention provides a method for reducing, inhibiting and/or treating infections, disease states or conditions which are caused by *Entamoeba histolytica*. These disease states and/or conditions include amoebiasis, amoebic dysentery, extraintestinal amoebiasis, amoebic liver abscess, amoeba cutis, and amoebic lung abscess. In this aspect, the method of the present invention comprises administering to a subject or patient in need an amount of a compound of the invention, the amount being sufficient to reduce, inhibit or cure infection and/or a disease state and/or condition caused by *Entamoeba histolytica* or *Acanthamoeba* spp. The compounds according to the present invention may be used alone or combined with another agent useful in treating infections caused by *Entamoeba histolytica* or *Acanthamoeba*, including metronidazole, bismuth subsalicylate, kaolin pectin, diphenoxyolate, loperamide, quinolones, erythromycin, trimethoprim-sulamethoxazole, ceftriaxine, ampicillin, tetracycline, doxycycline, vancomycin iodoquinol and mixtures thereof.

In the present invention, the method of treatment comprises administering to the subject in need of treatment, in a pharmaceutically acceptable carrier, an effective amount of a compound according to I below:

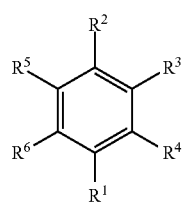

I

Wherein $R^1$ and $R^2$ are each independently H or a $C_1$-$C_3$ alkyl group;

$R^3$ is a

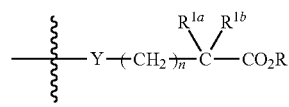

group,
where Y is absent, O or S;
n is 0, 1, 2, 3, 4, 5 or 6;
R is H, a $C_1$-$C_{20}$ alkyl group or a phenyl group optionally substituted with a hydroxyl, halo or $C_1$-$C_3$ alkyl group;
$R^{1a}$ and $R^{1b}$ are each independently H or a $CH_3$ group with the proviso that at least one of $R^{1a}$ and $R^{1b}$ is a methyl group; and
said

moiety is optionally substituted with a halo group (F, Cl, Br or I), a $C_1$-$C_3$ alkyl group or a hydroxyl group (preferably, the methylene group alpha to the carbon group containing the $R^{1a}$ and $R^{1b}$ substituents is substituted with a methyl or ethyl group);
$R^4$ is H or a $C_1$ to $C_4$ alkyl group;
$R^5$ is H, halo (F, Cl, Br or I), a $C_1$-$C_6$ linear or branch-chained alkyl group (preferably a $C_1$-$C_4$ alkyl group), a $C_1$-$C_6$ alkoxy group or a

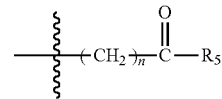

group where $R_5$ is an optionally substituted phenyl or a 5- or 6-membered heteroaryl group, or $R^5$, together with $R^6$, forms an optionally substituted phenyl group (preferably a $C_1$-$C_4$ alkoxy, e.g. methoxy or ethoxy substituted phenyl group) or an optionally substituted 5- or 6-membered heteroaryl ring (preferably, an oxazole ring, preferably substituted with a ortho- or para-halogen e.g. F, Cl, substituted phenyl group) thus forming a bicyclic ring system; and
$R^6$ is H, halo, $C_1$-$C_6$ linear or branch-chained alkyl group (preferably, a $C_1$-$C_4$ alkyl group), a $C_1$-$C_6$ alkoxy group or a

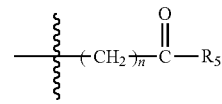

group where $R_5$ is an optionally substituted phenyl or a 5- or 6-membered heteroaryl group, or $R^6$, together with $R^5$, forms an optionally substituted phenyl group or an optionally substituted 5- or 6-membered heteroaryl ring, thus forming an optionally substituted bicyclic ring system, or a pharmaceutically acceptable salt, enantiomer, solvate or polymorph thereof.

In preferred aspects of the invention, $R^5$ and $R^6$ together form a phenyl group which is optionally substituted by at least one methoxy group (preferably, furthermost from the $R^3$ substituent as in naproxen, methallenestril and flunoxaprofen—see FIG. 10 hereof) and $R^4$ is H. In other aspects of the invention, $R^{1a}$ is methyl and $R^{1b}$ is hydrogen providing a chiral center and the possibility of racemic mixtures and individual enantiomers, each of which may be used in the present invention. In substituent $R^3$, n is preferably 0 or 1 and Y is absent. In alternative preferred embodiments, when $R^5$ and $R^6$ together form a phenyl or heteroaryl group, in the $R^3$ substitutent, Y is absent and n is 0 or 1 and when n is 1, the methylene group is substituted with a $C_1$-$C_3$ alkyl (preferably ethyl) and $R^{1a}$ and $R^{1b}$ are both methyl. When n is 0, only one of $R_{1a}$ and $R_{1b}$ is H, thus forming a chiral center. In alternative aspects of the invention where $R^5$ and $R^6$ do not form a ring to create a bicyclic group, Y in $R^3$ is preferably 0 or absent, n is 0, 1, 2, 3, or 4 (preferably 0 or 3), $R^{1a}$ is methyl and $R^{1b}$ is H (thus forming a chiral center). In these monocyclic embodiments, $R^5$ is H or a halogen group, preferably H, $R^6$ is H or a $C_1$-$C_6$ alkyl group (preferably H or a $C_3$ or $C_4$ linear or branch-chained alkyl group, $R^4$ is preferably H and $R^1$ and $R^2$ are H or $CH_3$, preferably H.

The alternative embodiments, the present invention relates to methods of treatment wherein the compound is selected from the group consisting of R-Naproxen, S-Naproxen, methallenestril, R-Flunoxaprofen, S-flunoxaprofen, R-Ibuprofen, S-Ibuprofen, S-Ketoprofen, R-Ketoprofen, gemfibrozil, ecabet, exetecan acid, R-Ketoralac, S-Ketoralac, tanomastat, mitiglinide, cicloxillic acid, fexofenadine, cilomilast, levocabastine, tiagabine, cinalukrast and mixtures thereof, including pharmaceutically acceptable salts, enantiomers, racemic mixtures, solvates and polymorphs thereof. A number of these compounds or their salts are presented in attached FIG. 10.

In the methods treating or inhibiting cancer or the metastasis of cancer, the compounds described above may be coadministered with at least one additional anticancer agent including, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H -pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(But)6,Azgly 10] (pyro-Glu-His-Trp-Ser-Tyr-D-Ser(But)-Leu-Arg-Pro-Azgly-$NH_2$acetate $[C_{59}H_{84}N_{18}Oi_4$-$(C_2H_4O_2)_2]_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951 aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11 dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others, and mixtures thereof.

In methods involving infections, disease states and/or conditions caused by *Entamoeba histolyltica* or *Acanthamoeba*, including amoebiasis, amoebic dysentery, extraintestinal amoebiasis, amoebic liver abscess, amoeba cutis, amoebic lung abscess and acanthmoebiasis of the eye (Acanthamoebia), at least one compound according to the present invention, alone or in combination with at least one further agent selected from the group consisting of metronidazole, bismuth subsalicylate, kaolin pectin, diphenoxyolate, loperamide, quinolones, erythromycin, trimethoprim-sulamethoxazole, ceftriaxine, ampicillin, tetracycline, doxycycline, vancomycin iodoquinol and mixtures thereof is administered in an effective amount to a patient of subject in need thereof.

The following examples illustrate but are not intended in any way to limit the invention.

Experimental Rationale and Approach

Figure 2:
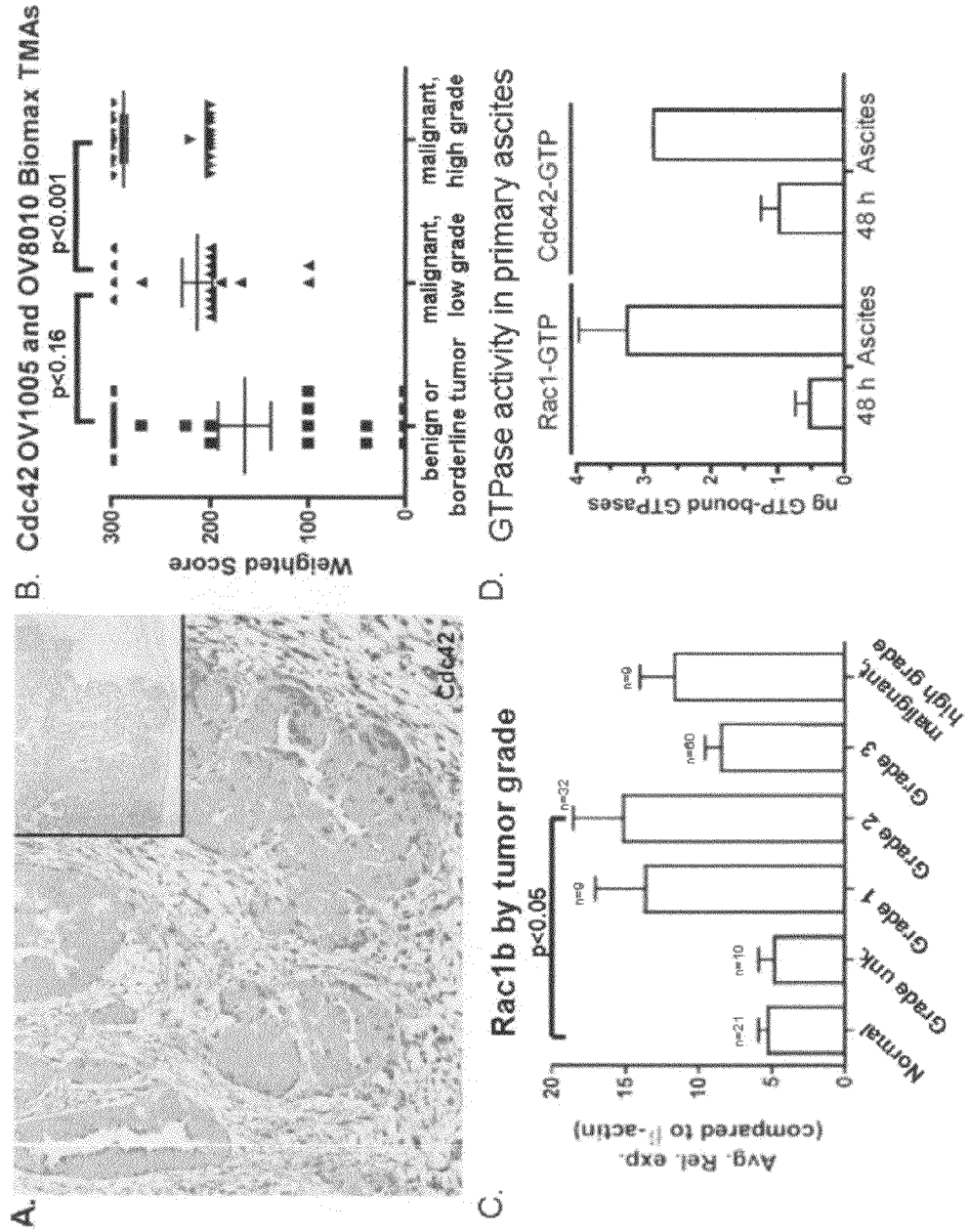
FIG. 2 shows dysregulation of GTPase targets: Elevated Cdc42 and Rac1b in human ovarian tumor samples. (A-B) Ovarian tumor tissue microarrays were purchased from US Biomax and stained for Cdc42 (pAb 10155-1-AP Protein-Tech Group, Inc.), inset shows low magnification view with less staining of adjacent normal tissue. Tumor grade and type was confirmed, and immunoreactivity scoring was determined. (B) Statistical analyses show p<0.001 for low vs. high grade tumors, Dr. E. Bedrick of the UNM Cancer Center Biostatistics core. (C) Primary tumor cDNA samples (TissueScan Disease Tissue qPCR Arrays, OriGene) were screened for Rac1b expression by qPCR. Normal vs. Gr. 2 p<0.05. (D) Rac1 and Cdc42 GTPase activities measured by GLISA in cells from fresh ovarian patient ascites or after 48 h in culture.

The Ras-homologous (Rho) family of small GTPases (Rac, Cdc42 and Rho) are key regulators of actin reorganization, cell motility, cell-cell and cell-extracellular matrix (ECM) adhesion as well as of cell cycle progression, gene expression and apoptosis (FIG. 1) [1-8]. In many human cancers (including colon and breast), aberrant Rho-family signaling due to changes in the GTPase itself or in its regulation loops is a critical underpinning of tumor growth and survival, invasion and metastasis [9-13] (FIG. 1). RhoA and RhoC correlate with advanced ovarian cancer and peritoneal dissemination [14; 15]. Our own studies are the first to demonstrate dysregulation of Rac1 and Cdc42 in ovarian tumor specimens (FIG. 2).

Figure 6:
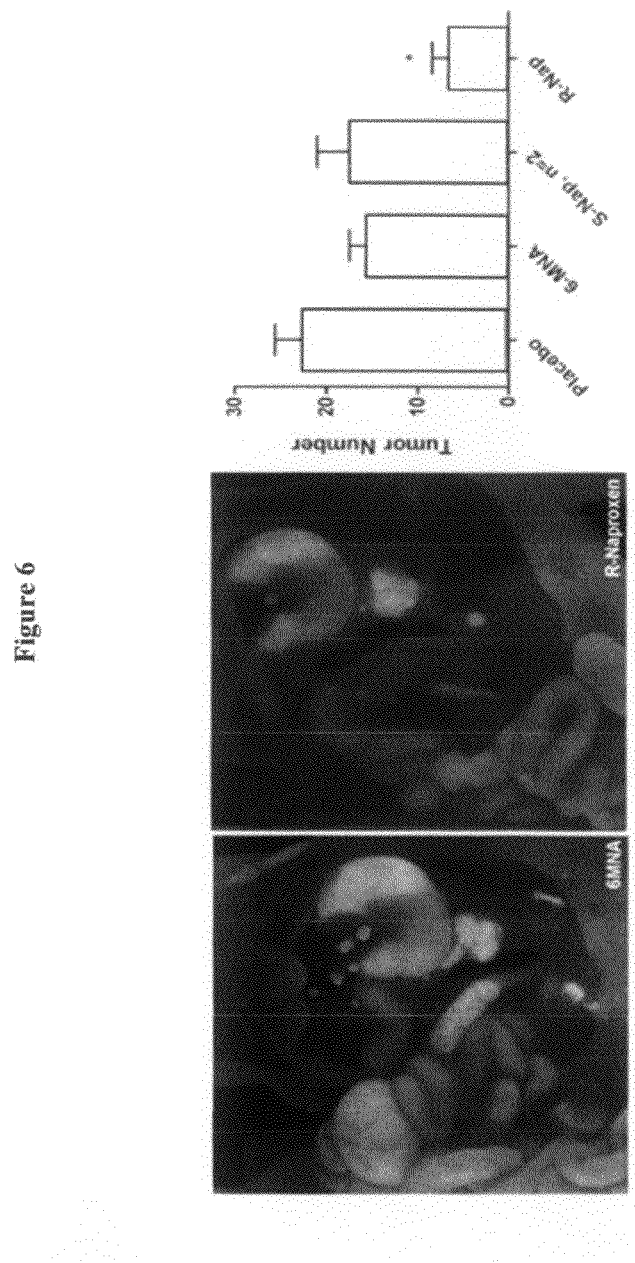
FIG. 6 shows that R-Naproxen reduces tumor number in xenograft model. Athymic nude mice were given an oral dose (10 mg/kg) of the indicated compounds in transgenic dough. Individual dosing was confirmed by direct observation. Mice were acclimated with placebo for 3 days and 1 day prior to injections of human ovarian GFP-tagged SKOV3ip cells, mice were left on placebo or provided the indicated treatments. After 2 weeks of tumor growth the mice were sacrificed, necropsy was performed and images were taken of the peritoneal cavity. All tumors were counted by moving internal organs with quantification given in the chart.

Although Rac1 and Cdc42 have been recognized as attractive therapeutic targets, specific Rac GTPase inhibitors while effective in culture [16; 17] have not been translated to clinical use and there are no established Cdc42 specific inhibitors. Lovastatin was shown to inhibit Rho GTPase and reduce ovarian metastasis in a xenograft model [15]. However, the use of statins to block GTPase membrane association has met with only modest success due to their broad spectrum inhibition of protein prenylation resulting in pleiotropic effects on many GTPases and pathways [18]. Thus, more specific agents for clinical application are urgently needed. The inventors identified two FDA approved drugs as inhibitors of Rac and Cdc42 that block ovarian cancer cell behaviors associated with tumor growth, dissemination and invasion (FIGS. 3-4) and display activity an intraperitoneal xenograft model (FIG. 6).

The studies described herein are significant for several reasons. First, the inventors investigate Rad and Cdc42 as therapeutic targets in ovarian cancer, a disease with limited treatment options. Effective targeting of key regulators of metastatic spread would have substantial positive impact on patient quality of life and duration of disease-free survival. Second, the inventors determine the mechanism of action of the novel Rac1 and Cdc42 inhibitors that will inform future development of targeted therapeutics. Third, testing FDA approved drugs for impact on ovarian cancer enable positive results to be rapidly translated to phase ½ clinical trials. Finally, results are expected to be applicable to numerous other cancers where Rac and Cdc42 and their downstream effectors are aberrantly activated.

Other disease states and conditions which are favorably impacted by the results which are obtained from the experiments described herein include the sporadic or genetic disease states and/or conditions in which Rho GTPases are implicated including, for example, Menkes disease, rheumatoid arthritis, atherosclerosis, diabetes (type I), Huntington's disease and Alzheimer's disease. Inhibition of GTPase is consistent with treatment modalities for these disease states and/or conditions which mediated through Rho GTPase.

High Throughput Screens

A first task involved conducting comprehensive high throughput screens for inhibitors and activators of small GTPases using purified proteins and libraries of both FDA approved and novel small molecules [19; 20]. Cheminformatics identified structure-activity relationships that allowed generation of testable, mechanistic hypotheses for Rac1 and Cdc42 inhibition by stereoisomeric compounds, including naproxen and ketorolac. The lack of activity by >20 other NSAIDs against GTPase targets strongly suggests enantiomer-selective targeting of Rac1 and Cdc42 by R-naproxen and R-ketorolac and related derivatives (FIG. 10). Although it has been long recognized that R-enantiomers of NSAIDS are poor inhibitors of COX activity and lack COX-associated toxicities [21-29], little is known about potential pharmacologic activities or targets of the R-enantiomers. In one example, R-etodolac has no COX inhibitory activity, but does retard tumor development and metastasis in a transgenic mouse model of prostate cancer [30]. The retinoid X receptor-α was identified as the R-etodolac target, indicating enantiomer-dependent selectivity for a novel target.

The discovery of the presently claimed compounds is based on high throughput screening, cheminformatics and direct biochemical and cellular testing showing that R-naproxen and R-ketorolac inhibit Rac1 and Cdc42 GTPase activities. Despite substantial evidence for a causal role of aberrant Rac1 and/or Cdc42 activity in human cancers, these proteins have not been widely explored as therapeutic targets. The limited numbers of small molecule Rac inhibitors (NSC23766 and derivatives, EHT 1864) disrupt specific activator proteins (i.e. GEFs) that convert the GTPase to the active state, or perturb effector coupling to block downstream signaling (FIG. 1) [16; 31-33].

Cheminformatic modeling of R-naproxen binding to Rac1 predicts the compound docks to an allosteric site in the nucleotide-binding pocket of the GDP-bound GTPase; suggesting a novel mechanism of action that is distinct from the current Rac inhibitors (FIG. 3) and the proposed studies may reveal a new avenue for disrupting Rac and Cdc42 activity. Although Rac1-targeted inhibitors display activity in cells and represent promising leads [16; 17; 33; 34], these compounds have not been translated to human use and Cdc42-specific inhibitors are not reported in the literature. In one aspect of the invention, the repurposing of FDA-approved drugs would offer a distinct advantage over new chemical entities requiring extensive toxicity and safety testing prior to clinical application. Thus, the R-enantiomers of naproxen and ketorolac (FDA approved in the racemic mixtures) and compounds listed in FIG. 10 offer an innovative approach for therapeutic targeting of Rac1 and Cdc42. The proposed studies provide critical information on the mechanism and feasibility of targeting Rac1 and Cdc42 with the R-enantiomers of naproxen and ketorolac. The expertise of the multi-disciplinary investigative team and collaborators (cheminformatics, bioinformatics, crystallography, biochemistry, cell biology and in vivo tumor modeling) fosters the advancement of these Rac1/Cdc42 targeted compounds with potential for rapid translation, and conversely validate Rac1 and Cdc42 as novel therapeutic targets in ovarian cancer.

Rationale and Feasibility of the Examples:

Ovarian cancer metastasis is predicted to be strongly dependent on Rac1/Cdc42-regulated pathways for exfoliation, formation of multicellular aggregates (MCAs), mesothelial adhesion, and localized invasion into the interstitial collagen-rich submesothelial matrix (FIG. 1) [35-38]. The preliminary data generated offer the first evidence for dysregulation of Rac1 and Cdc42 GTPase expression and activity in ovarian cancer (FIG. 2). Stage and grade dependent overexpression of Cdc42 and Rac1 proteins was based on immunohistochemical staining of human tumor samples. GTPase overexpression levels were highly significant for malignant, high-grade tumors (Rac1 (p=0.009) and Cdc42 (p<0.001)). Expression of a constitutively active splice variant Rac1b (first documented in breast tumors, [12]) was detected by qPCR and a GLISA activity assay showed both Cdc42 and Rac1 GTPases highly active in fresh tumor isolates. These data provide the foundation for further experiments which are provided to delineate the impact of Rac1 and Cdc42 on measures of ovarian cancer disease and patient outcomes. Because activated Rac1 and Cdc42 regulate cell motility, survival and proliferation through multiple effectors (FIG. 1), we also investigate the status of effector proteins associated with the tumor cell behaviors that are altered by Rac1 and Cdc42 inhibitors (Table 1, FIG. 4). This information delivers mechanistic insight into the contributions of Rac1 and Cdc42 pathways to ovarian cancer and identify key downstream effector pathways associated with this disease. Access to a repository of tumor samples that are linked to patient outcomes through the Human Tissue Repository of the UNM NCI funded Cancer Center is important to decipher these pathways.

Further Examples

Screening of the Prestwick library of FDA-approved molecules identified the R-enantiomer of naproxen as active against Rac1 and Cdc42, which was confirmed in cellular GLISA assays (FIG. 3A). R-, and S-ketorolac were identified for structure activity testing based on cheminformatics. Despite the common chemotype, S-naproxen and 6-MNA did not significantly inhibit Rac1 or Cdc42 indicating that GTPase inhibition is independent of the COX pathway. At nontoxic doses that are meaningful with respect to human serum levels at therapeutic doses Table 2 [39-47], the R-enantiomers of naproxen or ketorolac are more effective for inhibition of migration in SKOV3ip (FIG. 4A-B), OVCA 429 (not shown) and primary ovarian tumor cells isolated from ascites (not shown). The same structure activity relationship was observed for multicellular aggregate formation (FIG. 4C). Inhibition of proliferation did not exceed 50% with R-naproxen>S-naproxen or 6-MNA and little inhibition by R- or S-ketorolac (not shown). We tested >20 other common NSAIDS and did not detect inhibitory activity in vitro or in cells against Rac1 or Cdc42, nor any impact on ovarian cell migration or proliferation. Thus, from the structure activity relationships and selectivity, we conclude that the inhibitory actions of R-naproxen and R-ketorolac are due to an effect on novel Rac1 and Cdc42 GTPase targets as first revealed by the molecular library screen and predicted by cheminformatics.

Virtual docking predicts that R-naproxen, but not S-naproxen can bind the GDP-bound pocket of Rac1 (FIG. 3B). In the model R-naproxen is stabilized through favorable H-bonds with Thr17 and Asp57, as well as through interaction with magnesium via the naproxen carboxyl group. Interestingly, Thr17 is the mutated residue in dominant negative forms of Rac1. The model predicts stabilization of the inactive GDP-bound GTPase and provides a testable hypothesis for a novel mechanism of action and the enantiomer selective differences in activity. As predicted by the enantiomer-selective inhibition of Rac1 and Cdc42 activity, we find that R-naproxen and the established Rac1 inhibitor NSC23766 inhibit ovarian tumor cell proliferation, migration and MCA formation (FIG. 4A-C and data not shown) while S-naproxen and 6-MNA display little effect. Similarly, in an intraperitoneal xenograft model, animals administered R-naproxen displayed a 4-fold reduction in tumor number and a 36% decrease in total tumor burden while the S-naproxen and 6-MNA treated animals were similar to placebo controls (FIG. 6). These data demonstrate that the enantiomer-selective properties of R-naproxen are preserved in vivo.

Establishing the Consequences of Rac1 and Cdc42 Activation and Overexpression in Human Ovarian Tumors.

Preliminary data generated represent the first evidence for increased Cdc42 and Rac1 expression and activation in ovarian cancer, and support the hypothesis that dysregulated Rac1 and Cdc42 will lead to the activation of one or more effectors and pathways that have negative impact on ovarian cancer patient outcome. Because several effectors are reportedly elevated or activated in ovarian cancer, it is important to address whether effector activation is dependent or independent of Rac1 and Cdc42 dysregulation to gain insights into the potential therapeutic impact of targeting Rac1 and Cdc42. No such integrated analyses have been conducted in ovarian cancer or in other cancers where Rho-family GTPases are overexpressed.

Focus is on the four downstream effectors (Table 1) with key roles in tumor growth and metastasis (FIG. 1), In human cancers, p21 activated kinase (PAK) isoforms act as nuclear effectors and are critical for tumor angiogenesis, epithelial-mesenchymal transition and anchorage independent growth downstream of Rac1 and Cdc42 [36; 48], Elevated PAK1 levels are correlated with poor prognosis and aggressive ovarian cancers, making it an effector of particular interest [49; 50]. Cell-cell adhesion is modulated by active Rac1 and Cdc42 through IQGAP1-mediated disassembly of adherens junctions and nuclear translocation of beta catenin [38]. Rac/Cdc42/IQGAP1 are predicted to modify MCA formation and/or dispersal upon mesothelial contact. Mesothelial invasion and contact with the collagen-rich submesothelial matrix is likely mediated through WAVES and WASP effectors, which function in actin remodeling and invasion. Activated Rac1 is important for integrin-mediated lamellipodia formation, cell spreading, and tumor cell migration via WAVE3 [51-53], while Cdc42 is important for invadopodia-mediated invasion via WASP [37]. WAVE3 and WASP pathways are downstream of activated Rac1 and Cdc42, respectively, and is important for discriminating if one or both GTPase pathways are active, and identify if functional redundancies amplify invasion or if one pathway predominates over another. The initial focus on these specific effectors is based on the cellular functions disrupted by R-naproxen, R-ketorolac and the Rac1 inhibitor NSC23766 (FIG. 4-5) and tumor cell activities that are necessary for ovarian cancer metastatic success. Experiments are designed to test the hypothesis that comparative evaluation of a cohort of interrelated signaling molecules in patient tissue samples will demonstrate their utility individually or as a panel for serving as prognostic markers and provide supporting evidence for their use as therapeutic targets.

General Approach to Analysis:

Immunohistochemical (IHC) analysis of ovarian tumor tissue microarrays (TMAs) is conducted using commercially available sources and UNM-generated TMAs with associated patient information. IHC images are recorded using an Aperio system with options for training and automated quantification. Independent verification of tumor pathology and marker evaluation isconducted by Ob/Gyn certified pathologist Lomo and statistical analysis is performed by the UNM CRTC biostatistics core as in FIG. 2.

Pathway Activation:

Stain for the markers indicated above are performed using commercially available tumor microarrays with multiple cores per case (US Biomax). Marker expression and localization (nuclear, cytoplasmic, membrane) is assessed. For example, PAK1 activation through phosphorylation and nuclear translocation is postulated to be a prognostic marker in ovarian cancer based on its association with poor overall and disease-free survival and activation of angiogenesis [54] therefore localization is an important indicator of activation status. Scoring is conducted by two pathologists for the presence or absence of staining, localization and good correlation (within 1 quartile) with percent and intensity (0-3+) of epithelial staining. Staining intensity is dichotomized with high- or overexpression defined as above the median of the product of intensity times the percentage of epithelial cells stained. There are two levels of statistical analysis. First, the protein expression levels and/or distribution of each marker isanalyzed with respect to tumor stage and grade and ovarian carcinoma histotypes (serous, clear cell, endometrioid, and mucinous). This study will identify markers with the greatest correlation to tumor parameters (histotype and disease stage/grade). The second analysis is to evaluate PAK1/pPAK1, WAVE3, WASP and IQGAP1 protein expression levels and distribution as functions of Rac1 and/or Cdc42 activation or overexpression in serial sections. These experiments will identify effectors with the greatest correlation to GTPase activation status and whether GTPase activation and specific downstream pathways are coordinately activated.

Patient Outcome

Rac1, Cdc42 and downstream effectors identified as being linked to ovarian tumor stage or grade are further tested on tumor microarrays with linked patient outcome data. A duplicate core tissue microarray (TMA) of archival specimens from 45 patients with ovarian tumors of low malignant potential (LMP) and 89 patients with epithelial ovarian cancer (EOC) are used. This TMA was used to identify the novel estrogen receptor GPR30 as a predictor of poor survival in ovarian cancer [55]. Based on ANOVA analyses and 45% differences in expression levels, a power of 0.8 is achieved through the evaluation of 80 samples, which is within our sample collection. Marker expression or localization, defined as above or below the median (intensity in compartment×the percentage of positive epithelial cells), is used to correlate staining with predictors of adverse outcome and overall or disease free survival. Additional arrays are prepared as needed. These experiments are used to determine the prognostic potential of activated GTPase markers alone or in combination with downstream effector pathways.

Statistical Analysis.

Clinical results are analyzed statistically. Pearson correlation (r) are used to compare Rac1/Cdc42 staining intensity to that of other markers, and results are confirmed using Spearman correlation. For the remaining analyses, staining intensity is dichotomized with high- or overexpression defined as above the median of the product of intensity times the percentage of epithelial cells stained. For continuous demographic data that are not normally distributed and for clinical and pathological data, respectively, nonparametric Wilcoxon and Fisher's exact tests are used. The LIFETEST procedure is used to calculate survival curves, and differences in survival are compared using the Log-rank test. P values $\leq 0.05$ is considered statistically significant. To discern relationships between two target proteins (e.g. GTPase and specific effectors) exhibiting positive staining in matched samples we will stratify using the Nottingham Prognostic Index, which identifies risk using clinical and pathologic parameters groups, and then derive Cox proportional hazards and regression tree models. Training and validation sets are derived to test the ability to distinguish patients with poor outcomes from those with good or moderate outcomes and to calculate hazard ratios.

Results and Alternative Approaches

Figure 4:
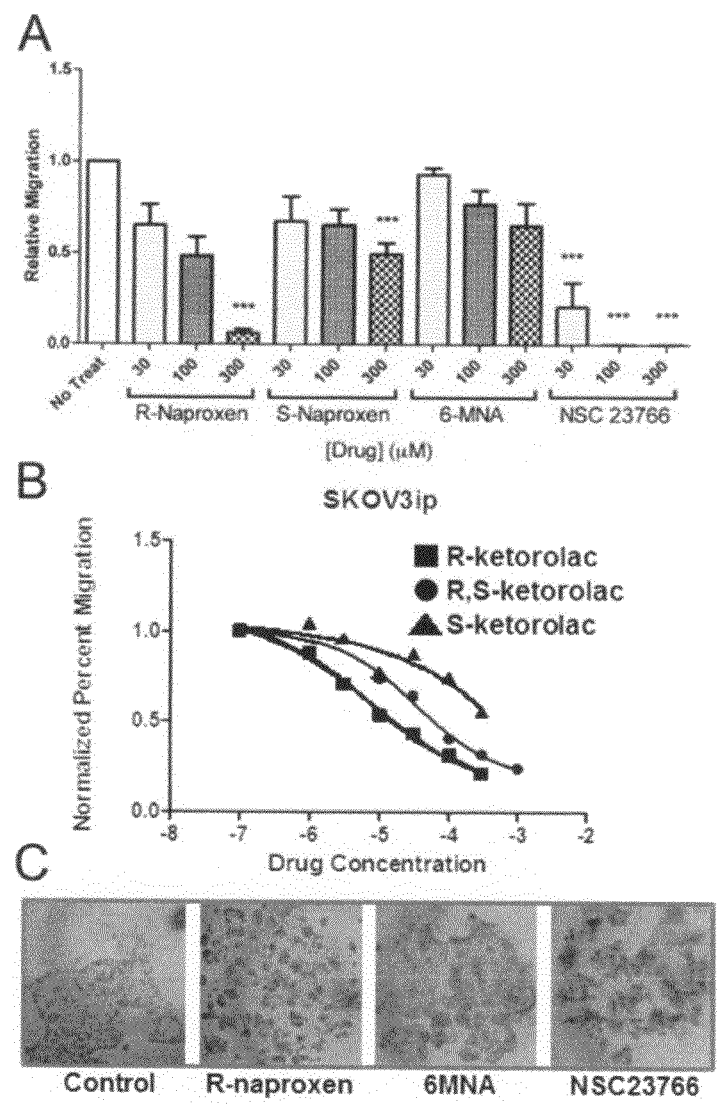
FIG. 4 shows enantiomer selective inhibition of ovarian tumor cell migration & aggregation. A) R-naproxen inhibits ovarian tumor cell migration. OVCA 429 cell migration was measured under the indicated conditions using modified Boyden chambers. *P<0.05 Similar results were obtained for SKOV3ip and OVCA 433 cells. (B) R-ketorolac inhibits ovarian tumor cell migration. SKOV3ip cells were incubated for 24 h under the indicated conditions and migration was measured as in (A). Comparable results were obtained for OVCA 429 cells. C) Inhibition of aggregation. OVCA 429 cells were trypsinized and resuspended at 3×106 cells/ml in medium containing drugs as indicated (100 µM). 25 µl drops were suspended and imaged after 24 h. Comparable responses were observed in OVCA 433 and SKOV3ip cells.
Figure 5:
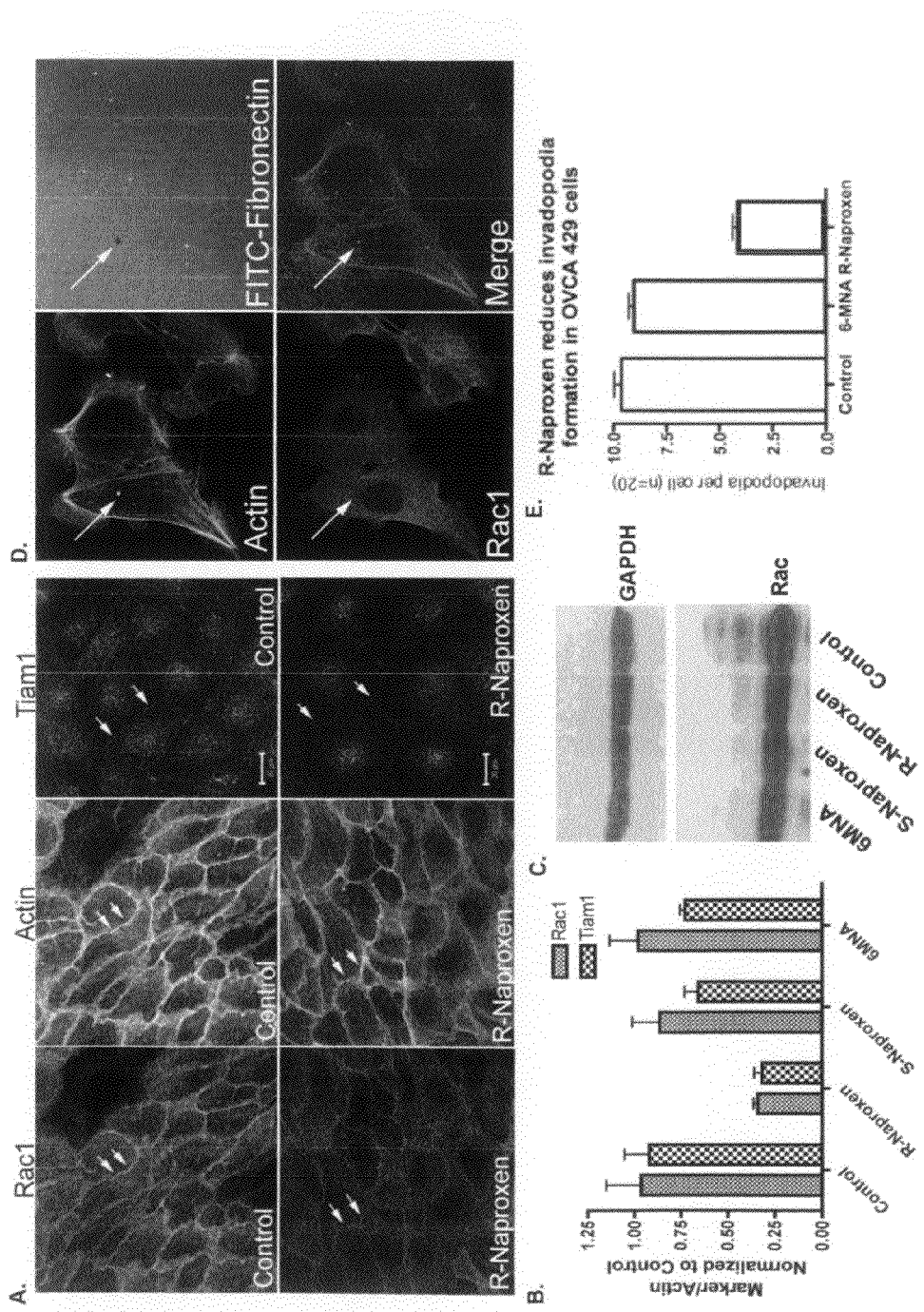
FIG. 5 shows certain assays of GTPase and pathway inactivation by drug treatment. (A) OVCA 433 cells were treated with 100 µM R-naproxen for 1 h, fixed and stained for Rac1, actin and TiamI. (B) Quantification of staining shows a notable loss of Rac1 and Tiam membrane association with R-naproxen, but not S-naproxen or 6MNA treatment. (C) Total Rac protein levels were unchanged by treatment. (D) OVCA 429 cells plated on FITC-fibronectin extend invadopodia into the matrix and create holes due to the activity of associated matrix metalloproteinases. (E) R-naproxen, but not 6MNA decreased invadopodia formation.

Rac1, Cdc42 and associated downstream effectors are predicted regulators of ovarian tumor cell growth and metastasis and we expect that in addition to predicting poor overall survival, one or both of the GTPases (Rac1/Cdc42) along with PAK1 (or pPAK1), WAVE3, WASP or IQGAP1 are associated with advanced stage and/or grade. If positive, we extend our studies to include analysis of matched primary tissue and metastatic lesions (US Biomax). Although our initial analysis of Rac1 and Cdc42 did not reveal significant differences in expression between serous and endometrioid tumors (not shown), it is possible that histotype associations are identified with one or more markers. For example, IQGAP activation leads to the disassembly of adherens junctions and nuclear translocation of beta catenin [38]. Analyses of nuclear beta-catenin identified a higher preponderance among endometriod as compared to serous carcinomas suggesting that activated beta-catenin might discriminate between ovarian cancer subtypes [56]. Each of the proposed markers has been tested in human tumor tissues. We use only antibodies that have been validated for IHC and conduct studies to optimize each marker individually. Additional tissues are available through the HTR is additional sample size is required to draw meaningful conclusions. PAK1 expression levels and altered distribution between nucleus and cytoplasm are important in tamoxifen resistant breast tumors and glioblastomas with poor prognosis [50; 57; 58]. Therefore, if PAK1 is a critical factor in ovarian cancer, expression is expected to be elevated and/or distribution between cytoplasm and nucleus may be altered in ovarian tumors as compared to normal tissues. As an alternative approach we look for altered PAK1 phosphorylation (correlated with poor outcome in glioblastoma) by western blot of primary tissue samples and taking into consideration best tissue procurement practices to preserve phosphoprotein profiles [58; 59]. WAVE3, if crucial in ovarian cancer, is expected to be increasingly expressed in the cytoplasm of ovarian tumor cells analogous to observations made for prostate cancer [51]. As surrogates for WAVE3 activation, matrix metalloproteases (MMP)-1 and -9, but not -2 should be upregulated and active. Diffuse overexpression of IQGAP1 is correlated with high-grade ovarian tumors, and overexpression and increased membrane association are also linked to gastric and hepatocellular carcinoma [60-62]. As a corollary to IQGAP activation, we expect to find elevated nuclear beta-catenin. RT QPCR may also be used as an alternate or in parallel to protein expression measures for marker validation. The outcomes from these studies will establish essential relationships between GTPase activation and corresponding downstream pathways that are related to ovarian tumor cell behavior linked to metastatic dissemination. Importantly, these cell behaviors are modulated by the R-enantiomers of naproxen and ketorolac and the Rac1 inhibitor NSC23766 (FIG. 4). The inventors thus identify those pathways with greatest likelihood of response to GTPase targeted therapeutics to be tested.

Determine the Mechanisms of Action of Small Molecule Inhibitors of Rac1/Cdc42 in Biochemical and Cell Based Assays.

Rationale:

Chemical Library Screens are conducted to identify inhibitors and activators of small GTPases [19]. Screening of the Prestwick chemical library of out-of-patent drugs identified the R-enantiomer of naproxen as active against Rac1 and Cdc42, which was confirmed in cellular assays; GLISAs that measure GTPase activation status (FIG. 3A), and proliferation, adhesion and migration assays that are reflective of pathways downstream of GTPase activation (FIG. 4). Using the Prestwick chemical library hit as a template, combined 2D- and 3D-based virtual screening techniques [63] to identify additional NSAIDs (not in the library) for testing was carried out. The nabumetone active metabolite, 6-MNA, ranked first on this list, as it shares a common chemotype with R- and S-naproxen. Since 6-MNA lacked Rac1 and Cdc42 activity (FIG. 3A and not shown), it was postulated that the rotational barrier around the carboxyl-substituted chiral center may explain differences in GTPase activity. Therefore the inventors performed additional similarity queries focused on a rotationally constrained carboxyl-substituted chiral center, and identified R- and S-ketorolac (also not in library) as matching enantiomeric candidates. R-ketorolac inhibited ovarian tumor cell migration with an $IC_{50}$ of ~10 µM (FIG. 4B).

Significant differences in the inhibitory activities of the naproxen series against GTPases were quantified (R-naproxen>S-naproxen>6-MNA) (FIG. 4A). The differences are thought to be a consequence of both rotational constraints around the chiral center imposed by the methyl group and a requirement for the aryl rings to be accommodated in a hydrophobic pocket that has a pyrrolizine that restricts rotation of a linked benzoyl ring. This is exemplified by recent crystallographic studies on naproxen binding to COX. S-naproxen displays optimal fit and inhibitory activity (50-70%) against COX enzymes based on crystallographic and enzymatic evaluations [22]. In contrast, R-naproxen displayed only 10-20% inhibition at >25 µM, which is explained based on the limited structural modification permitted by the NSAID binding pocket on COX enzymes [22]. In contrast to the COX enantiomeric specificity, virtual docking predicts R-naproxen, but not S-naproxen binding to the GDP-bound pocket of Rac1 (FIG. 3B). The model for R-naproxen binding to Rac1 predicts stabilization of the GDP-bound GTPase and provides a testable, novel mechanism for the inhibitory activities of the R-enatiomers of naproxen and ketorolac.

General Approach:

In vitro and cell based assays are conducted to: 1) establish the mechanism of naproxen and ketorolac inhibition using flow cytometry based equilibrium and kinetic assays; 2) monitor potential disruption of target interaction with GTPase regulatory and effector molecules in vitro; and 3) monitor drug treated cells for in vivo inhibition of pathways that are directly downstream of Rac1 and Cdc42 activation.

Testing of Compounds

Compounds for analysis are summarized in Table 2. Additional compounds are identified in FIG. 10. Each compound is tested in a log dose range corresponding to therapeutically relevant concentrations (average serum concentrations at standard dosing). The range for cell based testing of the naproxen series (R-, S- and 6MNA) is 10-300 µM; ketorolacs (R- and S-) is 1-30 µM and NSC 23766 10-100 µM (positive control for Rac1 inhibition). For in vitro assays the concentrations extend into the nanomolar range.

In Vitro Analyses of Nucleotide Binding to Determine Mechanism of Action.

A bead-based flow cytometry assay for measuring nucleotide binding is used to test the predicted novel mechanism of drug interaction with purified Rac1 and Cdc42 GTPases. Non-competitive and uncompetitive binding mechanisms of NSAIDs and other small molecules to protein active sties are well described in the literature [64-68]. BODIPY(4,4-difluoro-4-bora-3a,4a-diaza-s-indacene)-labeled nucleotide (GDP or GTP) binding to GSH-bead immobilized GST-Rac or GST-Cdc42 is quantitatively measured by flow cytometry as previously described [19; 69; 70]. Both equilibrium nucleotide binding in the presence or absence of increasing doses of each test compound (Table 2) and kinetics of nucleotide binding and dissociation with and without each compound is measured. The $K_d$ for BODIPY-GTP/GDP of Rac1 and Cdc42 is ~100 nM. Equilibrium competition experiments establish the $EC_{50}$ by testing serial dilutions of each compound across concentrations (0.03 nM-30 µM), while holding the concentration of BODIPY GTP/GDP constant around the $K_d$. Dissociation measurements under equilibrium conditions is performed by allowing BODIPY-nucleotide binding to saturation (90 min) and adding an excess of unlabeled nucleotide or drug and monitoring the dissociation rate of the bound nucleotide in real time. Kinetic experiments measure BODIPY-GTP/GDP on rates over ~250 s in the presence of compound concentrations well in excess of the $EC_{50}$. Off rates are determined by prebinding GTPase and BODIPY-GTP/GDP and adding compound in excess of $EC_{50}$ concentration. DMSO and excess unlabeled GTP/GDP controls are included in all experiments. Data are normalized and analyzed using Prism software as described in our published studies [19; 69; 70].

One of the predicted R-naproxen contact points is through a hydrogen bonding interaction with T17 of Rac1. Therefore, we test the impact of the classic dominant negative Rac T17N alone or in combination with D57A and D57N mutants on R-naproxen binding tested using BODIPY-GDP and flow cytometry as described above. Depending on the outcomes of the mechanism of inhibition studies on ketorolac, virtual docking studies is conducted and relevant site-directed mutants is generated as illustrated for R-naproxen (FIG. 3B).

These studies use the flow cytometry based GTP binding assay used for the initial HTS screen and characterization of other GTPase inhibitors [19; 69; 70], in establishing mechanism of drug interaction and in silico predictions of interactions to inform studies of protein:drug interaction [63; 76-84].

In Vitro Analyses of Drug Effects on Regulatory and Effector Protein Interactions with GTPases.

The virtual docking studies predict a novel mechanism of R-naproxen action (stabilizing inactive, GDP-bound state) relative to known Rac1 inhibitors that bind to the switch regions and block guanine nucleotide exchange factor interactions or promote nucleotide release [17; 33; 89]. GTPases have two switch regions that undergo significant conformational changes based on which nucleotide (GDP or GTP) is bound. Effector binding is restricted to the GTP-bound conformation thus we anticipate disruption of this interaction. In vitro Pak effector binding assays measure the inhibitory effects of drug binding on GTPase-effector protein interactions [90]. Purified His-Rac1 or His-Cdc42 is briefly preincubated (<15 min) with each test compound (0-100 µM), +/−GDP or $GTP_\gamma S$ addition. Recovery of GTPases in the active conformation is via PAK coated ELISA plates (Cytoskeleton, Inc.) and luminescent GTPase-specific antibody based readout or via addition of GST-PAK-PBD immobilized on GSH-beads followed by immunoblotting for bound GTPase fraction. Effects of naproxen and ketorolac on Tiam or Dbl GEF mediated activation of Rac1 and Cdc42, respectively, is measured using a kinetic, 96-well plate based mant-GTP binding assay in routine use in the lab. Tiam GEF is measured in the presence of ascorbyl stearate [91]. Dbl and reagents for GEF assay are purchased from Cytoskeleton, Inc. NSC23766 serves as a positive control for GEF inhibition.

Expected Results In Vitro Analysis:

The mechanism of inhibition of compounds according to the present invention are determined from flow cytometry experiments. In an uncompetitive inhibition mechanism the drug would bind only to the nucleotide-bound GTPase and thus would be expected to decrease the apparent $K_d$ and decrease the $B_{max}$. A noncompetitive inhibition mechanism would allow both the nucleotide and drug to bind simultaneously, but independently and thus without any change to the apparent $K_d$. However, since the bound inhibitor would block enzyme activity, $B_{max}$ should decrease. A competitive mechanism is considered unlikely, but would be associated with an increase in $K_d$ and no change in $B_{max}$. Both Rac1 and Cdc42 bind to the PAK effector protein. Binding assays in the presence of GDP and GTP alone will provide minimum and maximum binding activities. Binding in the presence of increasing doses of drugs will establish effects on regulatory and effector protein interactions. The composite studies lend insight into mechanism of action and inform plans for crystallographic analyses. One-way ANOVA of duplicates and repeated measures to 95% confidence intervals identify actives.

Small Molecule Impact on Effector Activity in Cells.

GLISA is extensively used for measuring EGF-stimulated Rac and Cdc42 activation in Swiss 3T3 cells in the presence and absence of test compounds. Preliminary data demonstrate R-naproxen inhibits Rac1 and Cdc42 GTPase activities in OvCA cell lines (429 and 433). However, direct GTPase inhibitory activity for the ketorolac series, although expected based upon the initial results, remains to be established. GLISAs in are highly specific, quantitative, can be performed with small sample sizes (<50 μs of cell lysate per assay, compared to 1-10 mg required for conventional PAK binding assay) and have excellent reproducibility. To assess the inhibitory effects of the small molecules in Table 2, preincubate cells for 15-60 min (times that establish detection of acute GTPase inhibition) with varying concentrations of each compound as described. NSC23766 serves as a positive control for Rac1 inhibition. The optimal time for measuring maximal EGF-stimulated Rac and Cdc42 activation in Swiss 3T3 cells and OVCA429 cells is after 2 min EGF treatment (FIG. 3A). Activated RhoA is also measured by GLISA following lysophosphatidic acid stimulation as an additional specificity control as needed. These analyses establish cellular IC50s (for R-naproxen and R-ketorolac relative to S-enantiomers and control compounds). Based on data, expectation of the enantiomer selectivity to be R>S, the reverse of what has been established for the COX enzymes [22].

As a mechanistic corollary to the inhibitory properties of R-naproxen and R-ketorolac on cell behaviors (proliferation, adhesion and migration, FIG. 4), it is of interest to determine which Rac1 and Cdc42 regulated pathways are directly affected by GTPase inhibition (FIG. 1, Table 1). Preliminary data demonstrate that R-naproxen, but not 6MNA treatment of OvCA cell lines inhibits Rac and Tiam membrane association consistent with the inhibition of Rac1 activity measured by GLISA (FIG. 5A-C). In addition, the formation of Cdc42-dependent, actin-based invadopodia that are crucial for matrix degradation and invasion [92; 93] is also significantly reduced by R-naproxen, but not by 6 MNA (FIG. 5D-E).

Using a combination of immunofluorescence staining, western blotting to monitor and quantify changes in localization, expression and phosphorylation of key downstream effectors of Rac1 and Cdc42+/− drug treatment (6-24 h) are monitored. The markers to be studied are the same as those that are monitored by IHC in tumor samples and allow direct testing of the impact of drug treatment on key pathways that are downstream of GTPase activation to gauge how well they are targeted by GTPase inhibition. Molecules/pathways analyzed include: a) membrane localization of GTPases (Rac1 and Cdc42) and regulatory proteins (Tiam1, Dbl GEFs) as measures of GTPase activation; b) IQGAP/beta catenin localization to adherens junction or nucleus as markers of stable cell-cell adhesion vs. EMT; c) PAK/pPAK as markers of pathways downstream of Rac1 and Cdc42 that alter proliferation and migration; d) WAVE and WASP membrane association in conjunction with lamellopodia and filopodia/invadopodia formation as measures of acute actin remodeling needed for cell migration and invasion. SiRNA knockdown of Rac1 and Cdc42 alone or in combination is used to verify that the drug responses depend on inhibition of Rac1 and Cdc42 function.

Expected Results and Alternatives:

The cell based assays identify which Rac1 and Cdc42 pathways are most directly impacted by GTPase inhibition and together with IHC results obtained in Aim1 provide mechanistic information about the pathways that are activated in ovarian cancer and can best be inhibited by small molecule GTPase inhibitors. In addition, the studies inform which measures are most useful for tracking molecular analyses of xenograft tissues as part of Aim 3. Requisite expertise in imaging and all the tools and assays needed for the study are routine as illustrated by data shown. Many commercial antibodies are available from different sources, thus, biochemical measures of phosphorylation or cell fractionation to establish changes in localization may be used as alternates. Statistics performed as for in vitro analyses.

Testing the Activity of Select NSAIDs in Preclinical Cell and Xenograft Animal Models.

Figure 7:
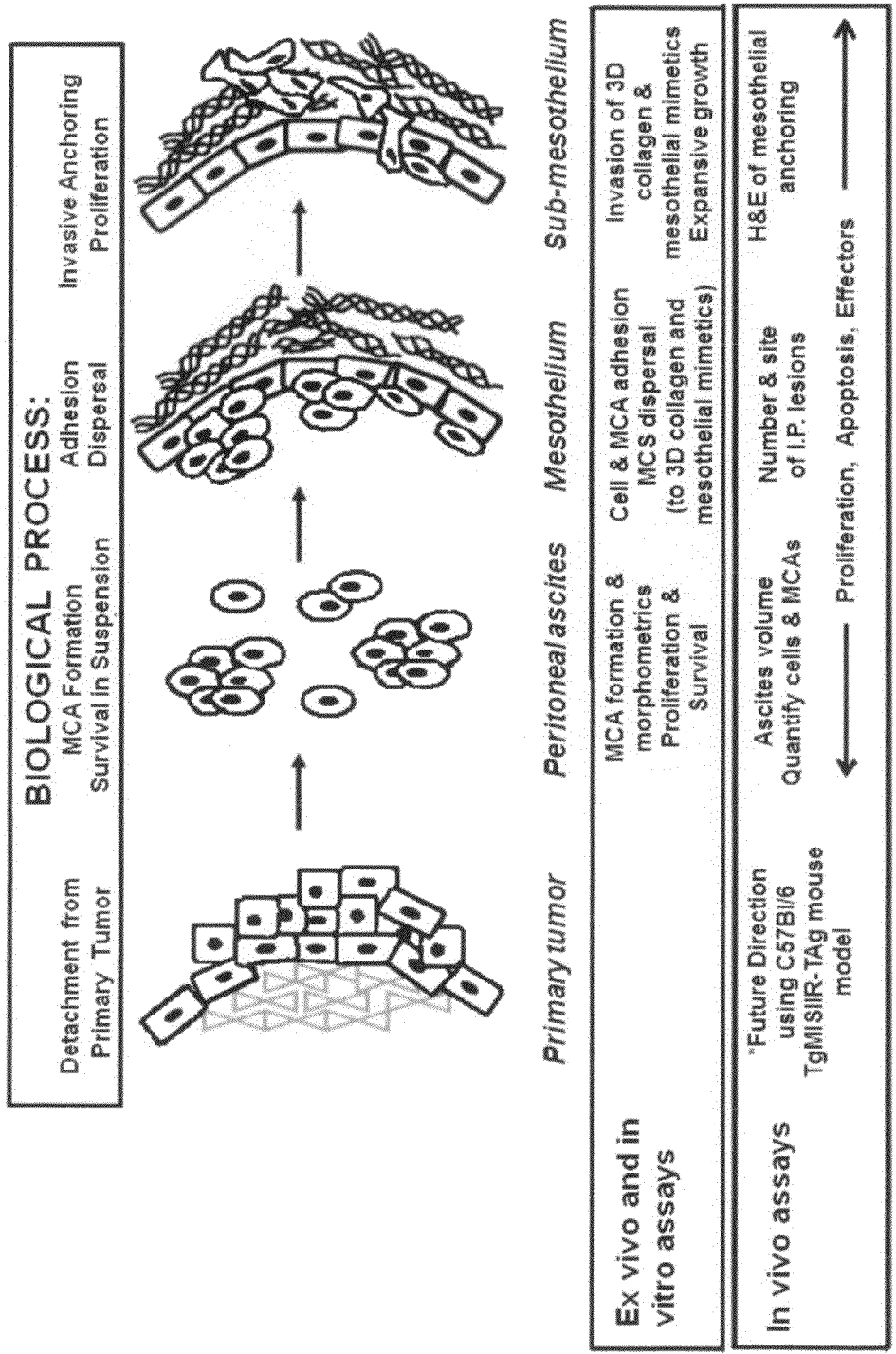
FIG. 7 shows biological processes involved in ovarian cancer metastasis. Rho family GTPases (Rac and Cdc42) contribute to metastatic dissemination and metastatic uccess as represented by survival of cells in ascites, mesothelial anchoring and invasion; these events are particularly relevant to residual and recurrent disease. MCA--multicellular aggregate.

The ovarian tumor microenvironment contains small molecules and ligands that stimulate signaling pathways upstream of Rac1 and Cdc42 (FIG. 1) [35; 94] and adhesive events required for peritoneal implantation and invasion also stimulate Rac1 and Cdc42 [95-102]. Therefore, it is believed that R-naproxen and R-ketorolac have demonstrable impact on biological processes required for ovarian cancer metastatic success (FIG. 7). In support of this hypothesis, R-naproxen decreased the number of implanted tumors in a xenograft animal model using athymic nude mice injected with human ovarian tumor cells adapted to intraperitoneal growth (SK-OVip; obtained through a formal MTA from MD Anderson). Treatments were incorporated into transgenic dough (BioServe, Frenchtown, N.J.) and animals were dosed twice per day to achieve established therapeutic serum levels [73]. Animals were given placebo dough or dough containing R-naproxen, S-naproxen or 6MNA. After sacrifice, animals fed R-naproxen exhibited a 4-fold reduction in tumor number (FIG. 6) and a 36% decrease in total tumor burden (not shown), while the 6MNA and S-naproxen treated animals were similar to the placebo controls. These data demonstrate that the enantiomer specific inhibitory properties of R-naproxen are preserved in vivo and that this NSAID may reduce tumor growth and spread, a point that is further tested and extended to ketorolac.

Additional Research:

An organotypic model is used to study the impact of small molecules on distinct components of ovarian tumor metastasis using cells derived from patients (ex vivo assays) and established ovarian tumor xenograft models (in vivo assays) (FIG. 6), Use of multiple ovarian cancer cell lines (429,433, Skov) and small molecule interventions defined in Table 2. Important questions regarding the biologic impact of small molecules on distinct aspects of ovarian tumor metastasis (see also FIG. 7) are answered:

1) R-Naproxen or Ketorolac Disrupts MCA Formation and Inhibits Ovarian Tumor Cell Proliferation and Survival in Suspension.

Metastatic cells are shed into the peritoneal cavity as single cells and spheroids or multicellular aggregates (MCAs) [103; 104] and because the majority of conventional chemotherapies are ineffective in preventing MCA growth and dissemination, they are considered a likely source of recurrent disease [105]. Disrupting MCA behavior is believed to represent an important therapeutic strategy.

2) The Small Molecules Interfere with Ovarian Tumor Cell Attachment and Invasive Anchoring to the Mesothelium Required for Metastatic Growth.

Aggregation and peritoneal attachment of multicellular aggregates (MCAs) is mediated via both β1-integrin and E-cadherin-dependent mechanisms [104; 106-112]. Rho-family GTPases are implicated in the establishment, maintenance and stability of cell:cell contacts and cadherin or CD44 engagement stimulates Rac1 and Cdc42 activity [95-102]. This illustrates the importance of testing small molecule inhibitors of Rac1/Cdc42 on cell:cell interactions that are meaningful for ovarian cancer metastasis.

Ex Vivo Studies:

The impact of novel small molecules on patient-derived tumor cells ex vivo is tested. Under an approved protocol, collection of tissues and ascites from patients with primary ovarian cancer is performed. The tissue is de-identified and the presence and type of tumor is verified histologically by a pathologist. Fresh tissue offers several distinct advantages to cell lines, namely the ability to 1) investigate dose-dependent response of primary ovarian tumor cells as a precursor to human translational studies, 2) directly relate target expression and activity with cell response to test compounds, and 3) establish whether the responses obtained in homogeneous established cell lines (FIG. 4) are replicated in the more relevant, heterogenous cell populations isolated from patients. OVCA 429 and SKOV3ip cells are included in parallel as these cells are used in xenograft models [113-117] for comparison between in vitro response and the in vivo correlates. Organotypic cultures and 3D collagen gels (3DCI) are used to model adhesive events that occur during intraperitoneal dissemination in vivo.

Functional Studies:

Ovarian ascites tumor cells are routinely maintained in short term culture with samples from ~35-75% of patients able to be established for ex vivo analysis [118]. Similarly, cultures can be developed from minced primary tumor tissue [119]. The epithelial nature of the cells is confirmed by EpCAM and HE4 antibody immunostaining. Only primary lines confirmed as greater than 80% epithelial tumor cells after enrichment are selected for analysis. Cell response −/+ the test compounds is cross-referenced to target expression and/or activity as in Aims 1-2, Standard experimental approaches which are used are demonstrated in the inventors' publications and preliminary findings [120-125]. Briefly, proliferation is measured by MTS assay, BrdU incorporation and cell counts; apoptosis by flow cytometry; migration and invasion by cell movement through a modified Boyden chamber without or with an artificial basement membrane, respectively; and cell aggregation/formation of MCA formation is evaluated in a hanging drop assay and MCA size and shape is analyzed by morphometric analysis [123]. Aggregate stability is estimated by subjecting MCAs to shear stress (trituration) followed by morphometric analysis [126]. MCAs are formalin fixed, paraffin embedded, sectioned and stained for active caspase-3 and -7 (BD Biosciences and Cell Signaling Technology, respectively) and cleaved PARP (Cell Signaling) or ApopTag reagents (Millipore). An apoptotic index is determined by quantifying the number of apoptotic cells as a fraction of the total cell number [127]. Control sections are stained with hematoxylin and eosin and Ki67 to quantify cell proliferation.

To more closely approximate adhesive events that occur during intraperitoneal dissemination in viva uses organotypic cultures [128]. Organotypic cultures and 3DCI gels are generated as previously described [35; 128-131]. Briefly, type I collagen gels with embedded fibroblasts are overlaid with a confluent layer of mesothelial cells (LP9) in 24 well plates or transwells containing a porous filter. Alternatively, 3DCI gels are evaluated in the absence of mesothelial cells to mimic mesothelial cell retraction and exposure of the underlying ECM. Adhesion and invasion of cells labeled using membrane permeable fluorescent dyes (CMFDA, Invitrogen) are enumerated using fluorescent microscopy [128; 131]. Expansive growth in 3D collagen is measured after cell growth for 6-10 d using morphometric analysis of proliferative aggregate dimensions and quantitation of the number and size invasive projections, as described previously [123].

Statistical Analysis.

Measurements are summarized using means, standard deviations (SD) and 95% confidence intervals (CIs). Categorical variables are summarized as percentages with 95% CIs. Box plots are used to informally compare groups and to check the normality assumption needed for parametric analyses. All tests are conducted at the 5% level. Multiple comparisons (i.e. Tukey's test) are used to quantify group differences when differences among groups are statistically significant. Analysis of variance (ANOVA) is used to compare means among treatment and control conditions when the basic unit of analysis is a measurement or an average. Analogous methods is used for counts (i.e. Poisson regression) and proportions (i.e. logistic regression for apoptotic index).

In Viva Studies

GFP-expressing OVCA 429 and SKOV3ip cells are used for the intraperitoneal (IP) xenograft studies (FIG. 6). The IP model will allow us to focus on adhesion and invasion in addition to tumor growth characteristics. Animals injected with SKOV3ip cells typically display ~20-30 metastatic implants at 20 days post implantation and animals succumb to disease at ~40 days with 80-100 overt peritoneal metastases [115]. Mice inoculated with OVCA 429 cells display a phenotype of large (>L5 $cm^3$) solid tumors that adhere loosely to fat in the pelvic region, intestine, and/or omentum in addition to multiple smaller tumors (<0.25 cm3) accumulating in the same three areas, with ascitic fluid accumulation [117]. Two treatment procedures are followed. 1) Introduce tumor cells and allow 7 days for the cells to engraft before treatment as a model of small molecule impact on residual disease. 2) Mice receive the intervention for two days before tumor cell inoculation to approximate the impact of small molecules on recurrent disease including tumor growth, metastatic implantation and invasive peritoneal lesions. The dose of R-naproxen, S-naproxen and 6-MNA is 20 mg/kg (oral) to approximate prescription dose levels in humans and these are common doses for naproxen treatment in mice [132-136]. Treatment of mice with 10 mg/kg S-naproxen led to plasma concentrations of ~94 µM within 3 h [137]. Ketorolac is dosed orally at 1 mg/kg to achieve serum levels comparable to human therapeutic doses [23; 75]. Based on published studies of in vivo NSC23766 administration, subcutaneous infusion via an osmotic minipump provides effective dosing [138; 139]. A dose of 10 mg/kg/day reduced Rac1 activity in the target tissue (kidney) without apparent evidence of organ toxicity in mice following 6 weeks of continuous dosing [139]. Saline administration via osmotic minipump serves as the control for NSC23766. These studies represent an extensive evaluation of drug action on growth and metastatic success, which has not been evaluated for naproxen or ketorolac or known Rac inhibitors in ovarian or other cancers.

Tumor Analysis

Tumor growth is estimated three times per week by weight and abdominal circumference in addition to GFP imaging using an IVIS Lumina II. At sacrifice ovarian tumor burden for each treatment condition is obtained by dissecting solid tumors from the peritoneal cavity, including tumor cell volume recovered from ascites and peritoneal washings [117]. Evaluate in some detail of tumor burden including ascites tumor, as well as metastatic events such as peritoneal adhesion and anchoring. Metastatic disease is to be scored based on pattern of spread, number, and size of secondary foci. Specifically, the number of lesions at each organ site (bowel, mesentery, pancreas, liver, diaphragm) is quantified and categorized as small (<1 mm), medium (1-2 mm) or large (>2 mm). In collaboration with Pathologist Lomo, tumor-containing abdominal tissues is fixed in formalin, paraffin embedded, sectioned and stained with H&E to enable scoring of the extent of invasion [117] on a 1-3 scale, where 1=non-invasive tumors with a smooth tumor-mesothelial interface, 2=moderately invasive with some infiltration of underlying tissue and 3=highly invasive, with significant submesothelial growth and evidence of desmoplastic host response [131].

Tumor Tissue Analysis

Excised tumors are evaluated for target enzyme inhibition, effector analysis, proliferation, apoptosis, and angiogenesis. Following sacrifice, tumor tissue is collected and then fixed in 10% phosphate-buffered formalin solution for immunohistology or snap frozen in liquid nitrogen then stored at −80° C. until analyzed. Tumor masses from and ascites cells is analyzed for GTPase activity by GLISA assay (Rac1, Cdc42), COX activity, proliferation index, apoptotic index, and mean vessel density. The GLISA assays have been used successfully in isolated tissues (Cytoskeleton, Inc) and would provide a direct measure of effective target inhibition. Alternatively, if greater tissue sample is required, Rac1 and Cdc42 activity is measured by Pak1 pull down assays from tumor lysates. COX activity is measured by ELISA. Proliferation and apoptotic indices based on tissue staining for Ki67 and TUNEL staining, respectively. The proliferation index is defined as percent cells positive for Ki67 in five randomly selected high power fields per tumor. Apoptotic index is determined by the number of apoptotic tumor cells in five randomly selected high-power fields exclusive of necrotic areas. Because COXs and Rho-family GTPases are involved in angiogenesis [140-148], we will measure mean vessel density (MVD) by counting CD31-positive vessels as described previously [149], Analyses of the expression and localization of downstream effectors (PAK1, WAVE3 and IQGAP1) as a function of drug treatment Statistical Analysis.

For animal studies, a 5% ANOVA test of no differences in means based on a sample of 8 per group has 82% (81%) power to detect a moderate effect size of 0.60 (0.63), where the effect size is given by the SD of the group means divided by the within group SD, Kaplan-Meier survival curves and log-rank tests is used to compare time to events. Repeated measures ANOVA are used to compare longitudinally measured in vivo growth parameters. Parametric or non-parametric ANOVA is used to compare tumor growth, immunochemistry and tissue measurements across groups at each time point. The mean number of lesions is compared across groups using ANOVA, treating the responses as Poisson counts. The extent of invasion and size of lesions are categorical responses and is compared across groups using chi-squared tests of homogeneity and logistic regression, respectively. Multiple lesions per site is handled using generalized estimating equations to give valid statistical tests that account for within-individual clustering. Tumor tissue measurements are summarized treated as for in vitro cell measurements.

Results and Alternative Approaches

The studies focus on the impact of identified small molecules on distinct mechanisms of metastasis in ovarian cancer (FIG. 7) and obtain detailed information adhesive events (cell:cell for MCAs or cell:mesothelium ex vivo and in vivo), invasion, growth and survival. Parallel experiments conducted in monolayer culture assess proliferation, apoptosis, migration, in vitro invasion and quantification of E-cadherin surface expression and endocytosis using techniques and approaches that are well documented in publications [121-125; 150; 151] to complement the findings obtained in 3D and organotypic models. Based on our preliminary findings, we predict that the R-enantiomers and NSC23776 will decrease MCA formation, cell migration and cell invasion because actin nucleation and polymerization are proximal targets for Rac1/Cdc42 through activation of effector molecules such as IQGAP & PAKs. However, MMPs are additionally required for invasion and COX activity is implicated in MMP expression [151] so 6MNA and the S-enantiomers may partially block invasive anchoring. We predict that the impact of small GTPase inhibition by NSC23766, R-naproxen or R-ketorolac will be most evident in the IP metastatic models where Rac1 and Cdc42 signaling play key roles in adhesive and actin-cytoskeleton-mediated events crucial to metastatic success (such as implantation and invasive lesions. The information on effective concentrations guides dose parameters for the future transition to Phase ½ clinical trials. If direct measurements of Rac1/Cdc42 activity in conjunction with effector activation reveal poor inhibition, we will adjust doses accordingly. While not all patient-based tumor cells will establish in short term culture or xenograft models, but with 60 cases/year the numbers are sufficient to validate the impact of the novel drugs on tumor-relevant endpoints. Promising results ex vivo and with tumor cell lines in vivo, will extend the studies to include IP xenograft studies using primary tumor cells from patients.

One concern is that S-ketorolac may cause gastrointestinal lesions in the course of the in vivo studies since these experiments will exceed the length of time recommended for human use of ketorolac. The GI toxicity in mice is dose dependent and low, but detectable at the proposed dose [23; 75]. Necropsy and histopathology are performed on any animals that succumb before conclusion of the tumor studies using services provided through the Cancer Center Animal Research Core. We do not anticipate problems with R-ketorolac because there is little interconversion between the R- and S-forms in rodents, and none detectable in humans [26]. Similarly, S-naproxen is not significantly subject to epimerization [29].

Because R-naproxen inhibits Rac1 and Cdc42, these studies will not clarify whether targeted inhibition of Rac1 or Cdc42 is more advantageous for antitumor activity in ovarian cancer. If antitumor activity is verified, follow up is with targeted knockdown of Rac1 or Cdc42 using Tet-inducible shRNA (ClonTech) or lentiviral approaches to compare the impact of targeting the GTPases singly or in combination. We recognize that as is true for all small molecules, the test compounds may have additional, as yet unidentified targets that could contribute to biologic response. By using positive controls for small GTPases (NSC23766, established Rac1 inhibitor), controls for response due to COX inhibition and incorporation of Rac1 or Cdc42 knockdown strategies we are able to address this possibility. In addition, a future goal is to test relevant small molecules in the TgMISIIR TAg mouse model of ovarian cancer to highlight potential impact on early disease.

SUMMARY

The experimental studies described herein represent the first efforts to investigate the potential of Rac1 and Cdc42 as therapeutic targets in metastatic ovarian cancer. The compounds identified, among others described, are FDA approved as the racemic mixture. Therefore, proof of concept that therapeutic targeting of Rac1 and/or Cdc42 confers antitumor benefit for ovarian cancer in vivo offer the potential for rapid clinical translation. An observational report notes that presurgical administration of R,S-ketorolac reduced cancer recurrence rates in breast cancer patients [152]. Thus, suggesting even short-term administration of racemic mixtures are of benefit. Establishing the R-enantiomers as drugs with novel targets combined with the possibility of obtaining R-enantiomer pure compounds for clinical studies through the NCI's Experimental Therapeutics (NExT) program will open new opportunities for drug development in a disease with limited options.

REFERENCES

1. Ellenbroek, S. I., and Collard, J. G. (2007) Rho GTPases: functions and association with cancer, *Clin Exp Metastasis* 24, 657-672.
2. Bosco, E. E., Mulloy, J. C., and Zheng, Y. (2009) Rac1 GTPase: a "Rac" of all trades, *Cell Mol Life Sci* 66, 370-374.
3. Heasman, S. J., and Ridley, A. J. (2008) Mammalian Rho GTPases: new insights into their functions from in vivo studies, *Nat Rev Mol Cell Biol* 9, 690-701.
4. Jaffe, A. B., and Hall, A. (2005) Rho GTPases: biochemistry and biology, *Annu Rev Cell Dev Biol* 21, 247-269.
5. Karlsson, R., Pedersen, E. D., Wang, Z., and Brakebusch, C. (2009) Rho GTPase function in tumorigenesis, *Biochim Biophys Acta* 1796, 91-98.
6. Ridley, A. J. (2006) Rho GTPases and actin dynamics in membrane protrusions and vesicle trafficking, *Trends Cell Biol* 16, 522-529.
7. Vega, F. M., and Ridley, A. J. (2008) Rho GTPases in cancer cell biology, *FEBS Lett* 582, 2093-2101,
8. Wennerberg, K., Rossman, K. L., and Der, C. J. (2005) The Ras superfamily at a glance, *J Cell Sci* 118, 843-846.
9. Fritz, G., and Kaina, B. (2006) Rho GTPases: promising cellular targets for novel anticancer drugs, *Curr Cancer Drug Targets* 6, 1-14.
10. Kamai, T., Yamanishi, T., Shirataki, H., Takagi, K., Asami, H., Ito, Y., and Yoshida, K. (2004) Overexpression of RhoA, Rac1, and Cdc42 GTPases is associated with progression in testicular cancer, *Clin Cancer Res* 10, 4799-4805.
11. Liu, Y., Wang, Y., Zhang, Y., Miao, Y., Zhao, Y., Zhang, P. X., Jiang, G. Y., Zhang, J. Y., Han, Y., Lin, X. Y., Yang, L. H., Li, Q. C., Zhao, C., and Wang, E. H. (2009) Abnormal expression of p120-catenin, E-cadherin, and small GTPases is significantly associated with malignant phenotype of human lung cancer, *Lung Cancer* 63, 375-382.
12. Schnelzer, A., Prechtel, D., Knaus, U., Dehne, K., Gerhard, M., Graeff, H., Harbeck, N., Schmitt, M., and Lengyel, E. (2000) Rac1 in human breast cancer: overexpression, mutation analysis, and characterization of a new isoform, Rac1b, *Oncogene* 19, 3013-3020.
13. Sun, D., Xu, D., and Zhang, B. (2006) Rac signaling in tumorigenesis and as target for anticancer drug development, *Drug Resist Updat* 9, 274-287.
14. Horiuchi, A., Imai, T., Wang, C., Ohira, S., Feng, Y., Nikaido, T., and Konishi, I. (2003) Up-regulation of small GTPases, RhoA and RhoC, is associated with tumor progression in ovarian carcinoma, *Lab Invest* 83, 861-870,
15. Horiuchi, A., Kikuchi, N., Osada, R., Wang, C., Hayashi, A., Nikaido, T., and Konishi, I. (2008) Overexpression of RhoA enhances peritoneal dissemination: RhoA suppression with Lovastatin may be useful for ovarian cancer, *Cancer Sci* 99, 2532-2539.
16. Ferri, N., Corsini, A., Bottino, P., Clerici, F., and Contini, A. (2009) Virtual screening approach for the identification of new Rac1 inhibitors, *J Med Chem* 52, 4087-4090.
17. Nassar, N., Cancelas, J., Zheng, J., Williams, D, A., and Zheng, Y. (2006) Structure-function based design of small molecule inhibitors targeting Rho family GTPases, *Curr Top Med Chem* 6, 1109-1116.
18. Sebti, S. M., and Hamilton, A. D. (2000) Farnesyltransferase and geranylgeranyltransferase I inhibitors in cancer therapy: important mechanistic and bench to bedside issues, *Expert Opin Investig Drugs* 9, 2767-2782.
19. Surviladze, Z., Waller, A., Wu, Y., Romero, E., Edwards, B. S., Wandinger-Ness, A., and Sklar, L. A. (2010) Identification of a small GTPase inhibitor using a high-throughput flow cytometry bead-based multiplex assay, *J Biomol Screen* 15, 10-20.
20. Agola, J. O., Surviladze, Z., Buranda, T., Ursu, O., Hong, L., Waller, A., Strouse, J. J., Simpson, D. S., Schroeder, C. E., Golden, J. E., Oprea, T. I., Sklar, L. A., and Wandinger-Ness, A. (2011) A Competitive Nucleotide Binding Inhibitor: In vitro Characterization of Rab? GTPase Inhibition, *ACS Chemical Biology Submitted,*
21. Carabaza, A., Cabre, F., Rotllan, E., Gomez, M., Gutierrez, M., Garcia, M. L., and Mauleon, D. (1996) Stereoselective inhibition of inducible cyclooxygenase by chiral nonsteroidal antiinflammatory drugs, *J Clin Pharmacol* 36, 505-512.
22. Duggan, K. C., Walters, M. J., Musee, J., Harp, J. M., Kiefer, J. R., Oates, J. A., and Marnett, L. J. (2010) Molecular basis for cyclooxygenase inhibition by the non-steroidal anti-inflammatory drug naproxen, *J Biol Chem* 285, 34950-34959.
23. Handley, D. A., Cervoni, P., McCray, J. E., and McCullough, J. R. (1998) Preclinical enantioselective pharmacology of (R)- and (S)-ketorolac, *J Clin Pharmacol* 38, 25S-35S.
24. Harman, C. A., Turman, M. V., Kozak, K. R., Marnett, L. J., Smith, W. L., and Garavito, R. M. (2007) Structural basis of enantioselective inhibition of cyclooxygenase-1 by S-alpha-substituted indomethacin ethanolamides, *J Biol Chem* 282, 28096-28105.
25. Janssen, A., Maier, T. J., Schiffmann, S., Coste, O., Seegel, M., Geisslinger, G., and Grosch, S. (2006) Evidence of COX-2 independent induction of apoptosis and cell cycle block in human colon carcinoma cells after 5- or R-ibuprofen treatment, *Eur J Pharmacol* 540, 24-33.
26. Jett, M. F., Ramesha, C. S., Brown, C. D., Chiu, S., Emmett, C., Voronin, T., Sun, T., O'Yang, C., Hunter, J. C., Eglen, R. M., and Johnson, R. M. (1999) Characterization of the analgesic and anti-inflammatory activities of ketorolac and its enantiomers in the rat, *J Pharmacol Exp They* 288, 1288-1297.

27. Kean, W. F., Lock, C. J., Rischke, J., Butt, R., Buchanan, W. W., and Howard-Lock, H. (1989) Effect of R and S enantiomers of naproxen on aggregation and thromboxane production in human platelets, *J Pharm Sci* 78, 324-327.
28. Suesa, N., Fernandez, M. F., Gutierrez, M., Rufat, M. J., Rotllan, E., Calvo, L., Mauleon, D., and Carganico, G. (1993) Stereoselective cyclooxygenase inhibition in cellular models by the enantiomers of ketoprofen, *Chirality* 5, 589-595.
29. Wechter, W. J. (1994) Drug chirality: on the mechanism of R-aryl propionic acid class NSAIDs. Epimerization in humans and the clinical implications for the use of racemates, *J Clin Pharmacol* 34, 1036-1042.
30. Kolluri, S. K., Corr, M., James, S. Y., Bernasconi, M., Lu, D., Liu, W., Cottam, H. B., Leoni, L. M., Carson, D. A., and Zhang, X. K. (2005) The R-enantiomer of the nonsteroidal antiinflammatory drug etodolac binds retinoid X receptor and induces tumor-selective apoptosis, *Proc Natl Acad Sci USA* 102, 2525-2530.
31. Vigil, D., Cherfils, J., Rossman, K. L., and Der, C. J. (2010) Ras superfamily GEFs and GAPs: validated and tractable targets for cancer therapy?, *Nat Rev Cancer* 10, 842-857.
32. Desire, L., Bourdin, J., Loiseau, N., Peillon, H., Picard, V., De Oliveira, C., Bachelot, F., Leblond, B., Taverne, T., Beausoleil, E., Lacombe, S., Drouin, D., and Schweighoffer, F. (2005) RAC 1 inhibition targets amyloid precursor protein processing by gamma-secretase and decreases Abeta production in vitro and in vivo, *J Biol Chem* 280, 37516-37525.
33. Shutes, A., Onesto, C., Picard, V., Leblond, B., Schweighoffer, F., and Der, C. J. (2007) Specificity and mechanism of action of EHT 1864, a novel small molecule inhibitor of Rac family small GTPases, *J Biol Chem* 282, 35666-35678.
34. Rosenblatt, A. E., Garcia, M. I., Lyons, L., Xie, Y., Maiorino, C., Desire, L., Slingerland, J., and Burnstein, K. L. (2011) Inhibition of the Rho GTPase, Rac1, decreases estrogen receptor levels and is a novel therapeutic strategy in breast cancer, *Endocr Relat Cancer* 18, 207-219.
35. Barbolina, M. V., Moss, N. M., Westfall, S. D., Liu, Y., Burkhalter, R. J., Marga, F., Forgacs, G., Hudson, L. G., and Stack, M. S. (2009) Microenvironmental regulation of ovarian cancer metastasis, *Cancer Treat Res* 149, 319-334.
36. Dummler, B., Ohshiro, K., Kumar, R., and Field, J. (2009) Pak protein kinases and their role in cancer, *Cancer Metastasis Rev* 28, 51-63.
37. Takenawa, T., and Miki, H. (2001) WASP and WAVE family proteins: key molecules for rapid rearrangement of cortical actin filaments and cell movement, *J Cell Sci* 114, 1801-1809.
38. White, C. D., Brown, M. D., and Sacks, D. B. (2009) IQGAPs in cancer: a family of scaffold proteins underlying tumorigenesis, *FEBS Lett* 583, 1817-1824.
39. Buckley, M. M., and Brogden, R. N. (1990) Ketorolac. A review of its pharmacodynamic and pharmacokinetic properties, and therapeutic potential, *Drugs* 39, 86-109.
40. Cohen, A., and Basch, C. (1988) Steady state pharmacokinetics of naproxen in young and elderly healthy volunteers, *Semin Arthritis Rheum* 17, 7-11.
41. Furst, D. E., Sarkissian, E., Blocka, K., Cassell, S., Dromgoole, S., Harris, E. R., Hirschberg, J. M., Josephson, N., and Paulus, H. E. (1987) Serum concentrations of salicylate and naproxen during concurrent therapy in patients with rheumatoid arthritis, *Arthritis Rheum* 30, 1157-1161.
42. Jung, D., Mroszczak, E., and Bynum, L. (1988) Pharmacokinetics of ketorolac tromethamine in humans after intravenous, intramuscular and oral administration, *Eur J Clin Pharmacol* 35, 423-425.
43. Kato, M., Nishida, S., Kitasato, H., Sakata, N., and Kawai, S. (2001) Cyclooxygenase-1 and cyclooxygenase-2 selectivity of non-steroidal anti-inflammatory drugs: investigation using human peripheral monocytes, *J Pharm Pharmacol* 53, 1679-1685.
44. Kendall, M. J., Chellingsworth, M. C., Jubb, R., Thawley, A. R., Undre, N. A., and Kill, D. C. (1989) A pharmacokinetic study of the active metabolite of nabumetone in young healthy subjects and older arthritis patients, *Eur J Clin Pharmacol* 36, 299-305.
45. Mroszczak, E. J., Jung, D., Yee, J., Bynum, L., Sevelius, H., and Massey, I. (1990) Ketorolac tromethamine pharmacokinetics and metabolism after intravenous, intramuscular, and oral administration in humans and animals, *Pharmacotherapy* 10, 33S-39S.
46. Pallapies, D., Peskar, B. A., Brune, K., and Geisslinger, G. (1994) Effects on platelet functions and pharmacokinetics of azapropazone and ketorolac tromethamine given as single parenteral doses, *Br J Clin Pharmacol* 37, 335-339.
47. Patrignani, P., Panara, M. R., Greco, A., Fusco, O., Natoli, C., Iacobelli, S., Cipollone, F., Ganci, A., Creminon, C., Maclouf, J., and et, a. (1994) Biochemical and pharmacological characterization of the cyclooxygenase activity of human blood prostaglandin endoperoxide synthases, *J Pharmacol Exp Ther* 271, 1705-1712.
48. Whale, A., Hashim, F. N., Fram, S., Jones, G. E., and Wells, C. M. (2011) Signalling to cancer cell invasion through PAK family kinases, *Front Biosci* 16, 849-864.
49. Brown, L. A., Kalloger, S. E., Miller, M. A., Shih, I., McKinney, S. E., Santos, J. L., Swenerton, K., Spellman, P. T., Gray, J., Gilks, C. B., and Huntsman, D. G. (2008) Amplification of 11 q 13 in ovarian carcinoma, *Genes Chromosomes Cancer* 47, 481-489.
50. Urzua, U., Best, L., and Munroe, D. J. (2010) Microarray proteomic analysis discriminates tumorigenic mouse ovarian surface epithelial cells of divergent aggressive potential, *Mol Biosyst* 6, 2521-2528.
51. Fernando, H. S., Sanders, A. J., Kynaston, H. G., and Jiang, W. G. (2010) WAVE3 is associated with invasiveness in prostate cancer cells, *Urol Oncol* 28, 320-327,
52. Sossey-Alaoui, K., Li, X., and Cowell, J. K. (2007) c-Abl-mediated phosphorylation of WAVE3 is required for lamellipodia formation and cell migration, *J Biol Chem* 282, 26257-26265.
53. Sossey-Alaoui, K., Ranalli, T. A., Li, X., Bakin, A. V., and Cowell, J. K. (2005) WAVE3 promotes cell motility and invasion through the regulation of MMP-1, MMP-3, and MMP-9 expression, *Exp Cell Res* 308, 135-145.
54. Siu, M. K., Wong, E. S., Chan, H. Y., Kong, D. S., Woo, N. W., Tam, K. F., Ngan, H. Y., Chan, Q. K., Chan, D. C., Chan, K. Y., and Cheung, A. N. (2010) Differential expression and phosphorylation of Pak1 and Pak2 in ovarian cancer: effects on prognosis and cell invasion, *Int J Cancer* 127, 21-31.
55. Smith, H. O., Arias-Pulido, H., Kuo, D. Y., Howard, T., Qualls, C. R., Lee, S. J., Verschraegen, C. F., Hathaway, H. J., Joste, N. E., and Prossnitz, E. R. (2009) GPR30 predicts poor survival for ovarian cancer, *Gynecol Oncol* 114, 465-471.
56. Madore, J., Ren, F., Filali-Mouhim, A., Sanchez, L., Kobel, M., Tonin, P. N., Huntsman, D., Provencher, D. M., and Mes-Masson, A. M. (2010) Characterization of the molecular differences between ovarian endometrioid carcinoma and ovarian serous carcinoma, *J Pathol* 220, 392-400.

57. Holm, C., Rayala, S., Jirstrom, K., Stal, O., Kumar, R., and Landberg, G. (2006) Association between Pak1 expression and subcellular localization and tamoxifen resistance in breast cancer patients, *J Natl Cancer Inst* 98, 671-680.
58. Aoki, H., Yokoyama, T., Fujiwara, K., Tani, A. M., Sawaya, R., Suki, D., Hess, K. R., Aldape, K. D., Kondo, S., Kumar, R., and Kondo, Y. (2007) Phosphorylated Pak1 level in the cytoplasm correlates with shorter survival time in patients with glioblastoma, *Clin Cancer Res* 13, 6603-6609.
59. Espina, V., Edmiston, K. H., Heiby, M., Pierobon, M., Sciro, M., Merritt, B., Banks, S., Deng, J., VanMeter, A. J., Geho, D. H., Pastore, L., Sennesh, J., Petricoin, E. F. r., and Liotta, L. A. (2008) A portrait of tissue phosphoprotein stability in the clinical tissue procurement process, *Mol Cell Proteomics* 7, 1998-2018.
60. Dong, P., Nabeshima, K., Nishimura, N., Kawakami, T., Hachisuga, T., Kawarabayashi, T., and Iwasaki, H. (2006) Overexpression and diffuse expression pattern of IQGAP1 at invasion fronts are independent prognostic parameters in ovarian carcinomas, *Cancer Lett* 243, 120-127.
61. Walch, A., Seidl, S., Hermannstadter, C., Rauser, S., Deplazes, J., Langer, R., von Weyhern, C. H., Sarbia, M., Busch, R., Feith, M., Gillen, S., Hofler, H., and Luber, B. (2008) Combined analysis of Rac1, IQGAP1, Tiam1 and E-cadherin expression in gastric cancer, *Mod Pathol* 21, 544-552.
62. White, C. D., Khurana, H., Gnatenko, D. V., Li, Z., Odze, R. D., Sacks, D. B., and Schmidt, V. A. (2010) IQGAP1 and IQGAP2 are reciprocally altered in hepatocellular carcinoma, *BMC Gastroenterol* 10, 125.
63. Bologa, C. G., Revankar, C. M., Young, S. M., Edwards, B. S., Arterburn, J. B., Kiselyov, A. S., Parker, M. A., Tkachenko, S. E., Savchuck, N. P., Sklar, L. A., Oprea, T. I., and Prossnitz, E. R. (2006) Virtual and biomolecular screening converge on a selective agonist for GPR30, *Nat Chem Biol* 2, 207-212.
64. Ault, A. (1974) An introduction to enzyme kinetics, *J Chem Educ* 51, 381-386.
65. Blat, Y. (2010) Non-competitive inhibition by active site binders, *Chem Biol Drug Des* 75, 535-540.
66. Fujita, K., Sugiyama, M., Akiyama, Y., Ando, Y., and Sasaki, Y. (2011) The small-molecule tyrosine kinase inhibitor nilotinib is a potent noncompetitive inhibitor of the SN-38 glucuronidation by human UGT1A1, *Cancer Chemother Pharmacol* 67, 237-241.
67. Rowlinson, S. W., Kiefer, J. R., Prusakiewicz, J. J., Pawlitz, J. L., Kozak, K. R., Kalgutkar, A. S., Stallings, W. C., Kurumbail, R. G., and Marnett, L. J. (2003) A novel mechanism of cyclooxygenase-2 inhibition involving interactions with Ser-530 and Tyr-385, *J Biol Chem* 278, 45763-45769.
68. Takahashi, Y., Hayashi, I., Tominari, Y., Rikimaru, K., Morohashi, Y., Kan, T., Natsugari, H., Fukuyama, T., Tomita, T., and Iwatsubo, T. (2003) Sulindac sulfide is a noncompetitive gamma-secretase inhibitor that preferentially reduces Abeta 42 generation, *J Biol Chem* 278, 18664-18670.
69. Schwartz, S. L., Tessema, M., Buranda, T., Pylypenko, O., Rak, A., Simons, P. C., Surviladze, Z., Sklar, L. A., and Wandinger-Ness, A. (2008) Flow cytometry for real-time measurement of guanine nucleotide binding and exchange by Ras-like GTPases, *Anal Biochem* 381, 258-266.
70. Tessema, M., Simons, P. C., Cimino, D. F., Sanchez, L., Waller, A., Posner, R. G., Wandinger-Ness, A., Prossnitz, E. R., and Sklar, L. A. (2006) Glutathione-S-transferase-green fluorescent protein fusion protein reveals slow dissociation from high site density beads and measures free GSH, *Cytometry A* 69, 326-334.
71. Pallapies, D., Salinger, A., Meyer zum Gottesberge, A., Atkins, D. J., Rohleder, G., Nagyivanyi, P., and Peskar, B. A. (1995) Effects of lysine clonixinate and ketorolac tromethamine on prostanoid release from various rat organs incubated ex vivo, *Life Sci* 57, 83-89.
72. Hinz, B., Cheremina, O., Besz, D., Zlotnick, S., and Brune, K. (2008) Impact of naproxen sodium at over-the-counter doses on cyclooxygenase isoforms in human volunteers, *Int J Clin Pharmacol Ther* 46, 180-186.
73. Huntjens, D. R., Spalding, D. J., Danhof, M., and Della Pasqua, 0. E. (2006) Correlation between in vitro and in vivo concentration-effect relationships of naproxen in rats and healthy volunteers, *Br J Pharmacol* 148, 396-404.
74. Kean, W. F., Lock, C. J., and Howard-Lock, H. E. (1991) Chirality in antirheumatic drugs, *Lancet* 338, 1565-1568.
75. Mroszczak, E., Combs, D., Chaplin, M., Tsina, I., Tarnowski, T., Rocha, C., Tam, Y., Boyd, A., Young, J., and Depass, L. (1996) Chiral kinetics and dynamics of ketorolac, *J Clin Pharmacol* 36, 521-539.
76. Edwards, B. S., Bologa, C., Young, S. M., Balakin, K. V., Prossnitz, E. R., Savchuck, N. P., Sklar, L. A., and Oprea, T. I. (2005) Integration of virtual screening with high-throughput flow cytometry to identify novel small molecule formylpeptide receptor antagonists, *Mol Pharmacol* 68, 1301-1310.
77. Edwards, 13. S., Young, S. M., Oprea, T. I., Bologa, C. G., Prossnitz, E. R., and Sklar, L. A. (2006) Biomolecular screening of formylpeptide receptor ligands with a sensitive, quantitative, high-throughput flow cytometry platform, *Nat Protoc* 1, 59-66.
78. Lloyd, D. G., Golfis, G., Knox, A. J., Fayne, D., Meegan, M. J., and Oprea, T. I. (2006) Oncology exploration: charting cancer medicinal chemistry space, *Drug Discov Today* 11, 149-159.
79. Olah, M. M., Bologa, C. G., and Oprea, T. I. (2004) Strategies for compound selection, *Curr Drug Discov Technol* 1, 211-220.
80. Oprea, T. I., Allu, T. K., Fara, D. C., Rad, R. F., Ostopovici, L., and Bologa, C. G. (2007) Lead-like, drug-like or "Pub-like": how different are they?, *J Comput Aided Mol Des* 21, 113-119.
81. Oprea, T. I., Tropsha, A., Faulon, J. L., and Rintoul, M. D. (2007) Systems chemical biology, *Nat Chem Biol* 3, 447-450.
82. Saunders, M. J., Graves, S. W., Sklar, L. A., Oprea, T. I., and Edwards, B. S. (2010) High-throughput multiplex flow cytometry screening for botulinum neurotoxin type a light chain protease inhibitors, *Assay Drug Dev Technol* 8, 37-46.
83. Taboureau, O., Nielsen, S. K., Audouze, K., Weinhold, N., Edsgard, D., Roque, F. S., Kouskoumvekaki, I., Bora, A., Curpan, R., Jensen, T. S., Brunak, S., and Oprea, T. I. (2011) ChemProt: a disease chemical biology database, *Nucleic Acids Res* 39, D367-72.
84. Winter, S. S., Lovato, D. M., Khawaja, H. M., Edwards, B. S., Steele, I. D., Young, S. M., Oprea, T. I., Sklar, L. A., and Larson, R. S. (2008) High-throughput screening for daunorubicin-mediated drug resistance identifies mometasone furoate as a novel ABCB1-reversal agent, *J Biomol Screen* 13, 185-193.
85. Eberth, A., Dvorsky, R., Becker, C. F., Beste, A., Goody, R. S., and Ahmadian, M. R. (2005) Monitoring the real-time kinetics of the hydrolysis reaction of guanine nucleotide-binding proteins, *Biol Chem* 386, 1105-1114.

86. Dvorsky, R., Blumenstein, L., Vetter, I. R., and Ahmadian, M. R. (2004) Structural insights into the interaction of ROCKI with the switch regions of RhoA, *J Biol Chem* 279, 7098-7104.
87. Hemsath, L., Dvorsky, R., Fiegen, D., Carlier, M. F., and Ahmadian, M. R. (2005) An electrostatic steering mechanism of Cdc42 recognition by Wiskott-Aldrich syndrome proteins, *Mol Cell* 20, 313-324.
88. Rose, R., Weyand, M., Lammers, M., Ishizaki, T., Ahmadian, M. R., and Wittinghofer, A. (2005) Structural and mechanistic insights into the interaction between Rho and mammalian Dia, *Nature* 435, 513-518.
89. Gao, Y., Dickerson, J. B., Guo, F., Zheng, J., and Zheng, Y. (2004) Rational design and characterization of a Rac GTPase-specific small molecule inhibitor, *Proc Natl Acad Sci USA* 101, 7618-7623.
90. Benard, V., and Bokoch, G. M. (2002) Assay of Cdc42, Rac, and Rho GTPase activation by affinity methods, *Methods Enzymol* 345, 349-359.
91. Crompton, A. M., Foley, L. H., Wood, A., Roscoe, W., Stokoe, D., McCormick, F., Symons, M., and Bollag, G. (2000) Regulation of Tiam1 nucleotide exchange activity by pleckstrin domain binding ligands, *J Biol Chem* 275, 25751-25759.
92. Fisher, K. E., Sacharidou, A., Stratman, A. N., Mayo, A. M., Fisher, S. B., Mahan, R. D., Davis, M. J., and Davis, G. E. (2009) MT1-MMP- and Cdc42-dependent signaling co-regulate cell invasion and tunnel formation in 3D collagen matrices, *J Cell Sci* 122, 4558-4569.
93. Machesky, L. M. (2008) Lamellipodia and filopodia in metastasis and invasion, *FEBS Lett* 582, 2102-2111.
94. Hudson, L. G., Zeineldin, R., Silberberg, M., and Stack, M. S. (2009) Activated epidermal growth factor receptor in ovarian cancer, *Cancer Treat Res* 149, 203-226.
95. Arulanandam, R., Vultur, A., Cao, J., Carefoot, E., Elliott, B. E., Truesdell, P. F., Larue, L., Feracci, H., and Raptis, L. (2009) Cadherin-cadherin engagement promotes cell survival via Rac1/Cdc42 and signal transducer and activator of transcription-3, *Mol Cancer Res* 7, 1310-1327.
96. Bourguignon, L. Y. (2008) Hyaluronan-mediated CD44 activation of RhoGTPase signaling and cytoskeleton function promotes tumor progression, *Semin Cancer Biol* 251-259.
97. Braga, V. M., and Yap, A. S. (2005) The challenges of abundance: epithelial junctions and small GTPase signalling, *Curr Opin Cell Biol* 17, 466-474.
98. Kothapalli, D., Flowers, J., Xu, T., Pure, E., and Assoian, R. K. (2008) Differential activation of ERK and Rac mediates the proliferative and anti-proliferative effects of hyaluronan and CD44, *J Biol Chem* 283, 31823-31829.
99. Murai, T., Miyazaki, Y., Nishinakamura, H., Sugahara, K. N., Miyauchi, T., Sako, Y., Yanagida, T., and Miyasaka, M. (2004) Engagement of CD44 promotes Rac activation and CD44 cleavage during tumor cell migration, *J Biol Chem* 279, 4541-4550.
100. Nelson, W. J. (2008) Regulation of cell-cell adhesion by the cadherin-catenin complex, *Biochem Soc Trans* 36, 149-155.
101. Samarin, S., and Nusrat, A. (2009) Regulation of epithelial apical junctional complex by Rho family GTPases, *Front Biosci* 14, 1129-1142.
102. Yamada, S., and Nelson, W. J. (2007) Localized zones of Rho and Rac activities drive initiation and expansion of epithelial cell-cell adhesion, *J Cell Biol* 178, 517-527.
103. Burleson, K. M., Boente, M. P., Pambuccian, S. E., and Skubitz, A. P. (2006) Disaggregation and invasion of ovarian carcinoma ascites spheroids, *J Transl Med* 4, 6.
104. Burleson, K. M., Casey, R. C., Skubitz, K. M., Pambuccian, S. E., Oegema, T. R. J., and Skubitz, A. P. (2004) Ovarian carcinoma ascites spheroids adhere to extracellular matrix components and mesothelial cell monolayers, *Gynecol Oncol* 93, 170-181.
105. Shield, K., Ackland, M. L., Ahmed, N., and Rice, G. E. (2009) Multicellular spheroids in ovarian cancer metastases: Biology and pathology, *Gynecol Oncol* 113, 143-148.
106. Casey, R. C., Burleson, K. M., Skubitz, K. M., Pambuccian, S. E., Oegema, T. R. J., Ruff, L. E., and Skubitz, A. P. (2001) Beta 1-integrins regulate the formation and adhesion of ovarian carcinoma multicellular spheroids, *Am J Pathol* 159, 2071-2080.
107. Casey, R. C., Oegema, T. R. J., Skubitz, K. M., Pambuccian, S. E., Grindle, S. M., and Skubitz, A. P. (2003) Cell membrane glycosylation mediates the adhesion, migration, and invasion of ovarian carcinoma cells, *Clin Exp Metastasis* 20, 143-152.
108. Green, S. K., Francia, G., Isidoro, C., and Kerbel, R. S. (2004) Antiadhesive antibodies targeting E-cadherin sensitize multicellular tumor spheroids to chemotherapy in vitro, *Mol Cancer Ther* 3, 149-159.
109. L'Esperance, S., Bachvarova, M., Tetu, B., Mes-Masson, A. M., and Bachvarov, D. (2008) Global gene expression analysis of early response to chemotherapy treatment in ovarian cancer spheroids, *BMC Genomics* 9, 99.
110. Lessan, K., Aguiar, D. J., Oegema, T., Siebenson, L., and Skubitz, A. P. (1999) CD44 and beta1 integrin mediate ovarian carcinoma cell adhesion to peritoneal mesothelial cells, *Am J Pathol* 154, 1525-1537.
111. Li, C. Z., Liu, B., Wen, Z. Q., and Li, H. Y. (2008) Inhibition of CD44 expression by small interfering RNA to suppress the growth and metastasis of ovarian cancer cells in vitro and in vivo, *Folia Biol (Praha)* 54, 180-186.
112. Strobel, T., and Cannistra, S. A. (1999) Beta1-integrins partly mediate binding of ovarian cancer cells to peritoneal mesothelium in vitro, *Gynecol Oncol* 73, 362-367.
113. Arlt, M. J., Novak-Hofer, I., Gast, D., Gschwend, V., Moldenhauer, G., Grunberg, J., Honer, M., Schubiger, P. A., Altevogt, P., and Kruger, A. (2006) Efficient inhibition of intra-peritoneal tumor growth and dissemination of human ovarian carcinoma cells in nude mice by anti-L1-cell adhesion molecule monoclonal antibody treatment, *Cancer Res* 66, 936-943.
114. Huang, S., Robinson, J. B. Deguzman, A., Bucana, C. D., and Fidler, I. J. (2000) Blockade of nuclear factor-kappaB signaling inhibits angiogenesis and tumorigenicity of human ovarian cancer cells by suppressing expression of vascular endothelial growth factor and interleukin 8, *Cancer Res* 60, 5334-5339.
115. Lotan, T., Hickson, J., Souris, J., Huo, D., Taylor, J., Li, T., Otto, K., Yamada, S. D., Macleod, K., and Rinker-Schaeffer, C. W. (2008) c-Jun NI-12-terminal kinase activating kinase 1/mitogen-activated protein kinase kinase 4-mediated inhibition of SKOV3ip.1 ovarian cancer metastasis involves growth arrest and p21 up-regulation, *Cancer Res* 68, 2166-2175.
116. Novak-Hofer, I., Cohrs, S., Grunberg, J., Friedli, A., Schlatter, M. C., Pfeifer, M., Altevogt, P., and Schubiger, P. A. (2008) Antibodies directed against L1-CAM synergize with Genistein in inhibiting growth and survival pathways in SKOV3ip human ovarian cancer cells, *Cancer Lett* 261, 193-204.
117. Shaw, T. J., Senterman, M. K., Dawson, K., Crane, C. A., and Vanderhyden, B. C. (2004) Characterization of intraperitoneal, orthotopic, and metastatic xenograft models of human ovarian cancer, *Mol Ther* 10, 1032-1042.
118. Metcalf, K. S., Selby, P. J., Trejdosiewicz, L, K., and Southgate, J. (1998) Culture of ascitic ovarian cancer cells as a clinically-relevant ex vivo model for the assessment of biological therapies, *Eur J Gynaecol Oncol* 19, 113-119.
119. Hassan, R., Lerner, M. R., Benbrook, D., Lightfoot, S. A., Brackett, D. J., Wang, Q. C., and Pastan, I. (2002) Antitumor activity of SS(dsFv)PE38 and SSI(dsFv)PE38, recombinant antimesothelin immunotoxins against human gynecologic cancers grown in organotypic culture in vitro, *Clin Cancer Res* 8, 3520-3526.
120. Cowden Dahl, K. D., Dahl, R., Kruichak, J. N., and Hudson, L. G. (2009) The epidermal growth factor receptor responsive miR-125a represses mesenchymal morphology in ovarian cancer cells, *Neoplasia* 11, 1208-1215.
121. Cowden Dahl, K. D., Symowicz, J., Ning, Y., Gutierrez, E., Fishman, D. A., Adley, B. P., Stack, M. S., and Hudson, L, G. (2008) Matrix metalloproteinase 9 is a mediator of epidermal growth factor-dependent e-cadherin loss in ovarian carcinoma cells, *Cancer Res* 68, 4606-4613.
122. Cowden Dahl, K. D., Zeineldin, R., and Hudson, L. G. (2007) PEA3 is necessary for optimal epidermal growth factor receptor-stimulated matrix metalloproteinase expression and invasion of ovarian tumor cells, *Mol Cancer Res* 5, 413-421.
123, Moss, N. M., Barbolina, M. V., Liu, Y., Sun, L., Munshi, H. G., and Stack, M. S. (2009) Ovarian cancer cell detachment and multicellular aggregate formation are regulated by membrane type 1 matrix metalloproteinase: a potential role in I.p. metastatic dissemination, *Cancer Res* 69, 7121-7129.
124. Symowicz, J., Adley, B. P., Gleason, K. J., Johnson, J. J., Ghosh, S., Fishman, D. A., Hudson, L. G., and Stack, M. S. (2007) Engagement of collagen-binding integrins promotes matrix metalloproteinase-9-dependent E-cadherin ectodomain shedding in ovarian carcinoma cells, *Cancer Res* 67, 2030-2039.
125. Zeineldin, R., Rosenberg, M., Ortega, D., Buhr, C., Chavez, M. G., Stack, M. S., Kusewitt, D. F., and Hudson, L. G. (2006) Mesenchymal transformation in epithelial ovarian tumor cells expressing epidermal growth factor receptor variant III, Mol Carcinog 45, 851-860.
126. Getsios, S., Amargo, E. V., Dusek, R. L., Ishii, K., Sheu, L., Godsel, L. M., and Green, K. J. (2004) Coordinated expression of desmoglein 1 and desmocollin 1 regulates intercellular adhesion, *Differentiation* 72, 419-433.
127. Bressenot, A., Marchal, S., Bezdetnaya, L., Garnier, J., Guillemin, F., and Plenat, F. (2009) Assessment of apoptosis by immunohistochemistry to active caspase-3, active caspase-7, or cleaved PART' in monolayer cells and spheroid and subcutaneous xenografts of human carcinoma, *J Histochem Cytochem* 57, 289-300.
128. Kenny, H. A., Krausz, T., Yamada, S. D., and Lengyel, E. (2007) Use of a novel 3D culture model to elucidate the role of mesothelial cells, fibroblasts and extra-cellular matrices on adhesion and invasion of ovarian cancer cells to the omentum, *Int J Cancer* 121, 1463-1472.
129. Barbolina, M. V., Adley, 13, P., Ariztia, E. V., Liu, Y., and Stack, M. S. (2007) Microenvironmental regulation of membrane type 1 matrix metalloproteinase activity in ovarian carcinoma cells via collagen-induced EGR1 expression, *J Biol Chem* 282, 4924-4931.
130. Barbolina, M. V., Adley, B. P., Kelly, D. L., Fought, A. J., Scholtens, D. M., Shea, L. D., and Stack, M. S. (2008) Motility-related actinin alpha-4 is associated with advanced and metastatic ovarian carcinoma, *Lab Invest* 88, 602-614.
131. Kenny, H. A., Dogan, S., Zillhardt, M., K Mitra, A., Yamada, S. D., Krausz, T., and Lengyel, E. (2009) Organotypic models of metastasis: A three-dimensional culture mimicking the human peritoneum and omentum for the study of the early steps of ovarian cancer metastasis, *Cancer Treat Res* 149, 335-351.
132. Efstathiou, J. A., Sampson, D. A., Levine, Z., Rohan, R. M., Zurakowski, D., Folkman, J., D'Amato, R. J., and Rupnick, M. A. (2005) Nonsteroidal antiinflammatory drugs differentially suppress endometriosis in a murine model, *Fertil Steril* 83, 171-181.
133. Greene, A. K., Alwayn, I. P., Nose, V., Flynn, E., Sampson, D., Zurakowski, D., Folkman, J., and Puder, M. (2005) Prevention of intra-abdominal adhesions using the antiangiogenic COX-2 inhibitor celecoxib, *Ann Surg* 242, 140-146.
134. Kendig, E. L., Schneider, S. N., Clegg, D. J., Genter, M. B., and Shertzer, H. G. (2008) Over-the-counter analgesics normalize blood glucose and body composition in mice fed a high fat diet, *Biochem Pharmacol* 76, 216-224.
135. Kumari, B., Kumar, A., and Dhir, A. (2007) Protective effect of non-selective and selective COX-2-inhibitors in acute immobilization stress-induced behavioral and biochemical alterations, *Pharmacol Rep* 59, 699-707.
136. Silakova, J. M., Hewett, J. A., and Hewett, S. J. (2004) Naproxen reduces excitotoxic neurodegeneration in vivo with an extended therapeutic window, *J Pharmacol Exp Ther* 309, 1060-1066.
137. Metzner, J., Popp, L., Marian, C., Schmidt, R., Manderseheid, C., Renne, C., Fisslthaler, B., Fleming, I., Busse, R., Geisslinger, G., and Niederberger, E. (2007) The effects of COX-2 selective and non-selective NSAIDs on the initiation and progression of atherosclerosis in ApoE −/− mice, *J Mol Med* 85, 623-633.
138. Muller, L. U., Schore, R. J., Zheng, Y., Thomas, E. K., Kim, M. O., Cancelas, J. A., Gu, Y., and Williams, D. A. (2008) Rac guanosine triphosphatases represent a potential target in AML, *Leukemia* 22, 1803-1806.
139. Shibata, S., Nagase, M., Yoshida, S., Kawarazaki, W., Kurihara, H., Tanaka, H., Miyoshi, J., Takai, Y., and Fujita, T. (2008) Modification of mineralocorticoid receptor function by Rac1 GTPase: implication in proteinuric kidney disease, *Nat Med* 14, 1370-1376.
140. Bryan, B. A., and D'Amore, P. A. (2007) What tangled webs they weave: Rho-GTPase control of angiogenesis, *Cell Mol Life Sci* 64, 2053-2065.
141. de Souza Pereira, R. (2009) Selective cyclooxygenase-2 (COX-2) inhibitors used for preventing or regressing cancer, *Recent Pat Anticancer Drug Discov* 4, 157-163.
142. Fryer, B. H., and Field, J. (2005) Rho, Rac, Pak and angiogenesis: old roles and newly identified responsibilities in endothelial cells, *Cancer Lett* 229, 13-23.
143. Fukumura, D., and Jain, R. K. (2007) Tumor microvasculature and microenvironment: targets for anti-angiogenesis and normalization, *Microvasc Res* 74, 72-84,
144. Ingber, D. E. (2008) Can cancer be reversed by engineering the tumor microenvironment?, *Semin Cancer Biol* 18, 356-364.
145. Mammoto, A., Mammoto, T., and Ingber, D. E. (2008) Rho signaling and mechanical control of vascular development, *Curr Opin Hematol* 15, 228-234.
146. Sarkar, F. H., Adsule, S., Li, Y., and Padhye, S. (2007) Back to the future: COX-2 inhibitors for chemoprevention and cancer therapy, *Mini Rev Med Chem* 7, 599-608.

147. Ushio-Fukai, M., and Nakamura, Y. (2008) Reactive oxygen species and angiogenesis: NADPH oxidase as target for cancer therapy, *Cancer Lett* 266, 37-52.
148. Wang, M. T., Honn, K. V., and Nie, D. (2007) Cyclooxygenases, prostanoids, and tumor progression, *Cancer Metastasis Rev* 26, 525-534.
149. Lin, Y. G., Kunnumakkara, A. B., Nair, A., Merritt, W. M., Han, L. Y., Armaiz-Pena, G. N., Kamat, A. A., Spannuth, W. A., Gershenson, D. M., Lutgendorf, S. K., Aggarwal, B. B., and Sood, A. K. (2007) Curcumin inhibits tumor growth and angiogenesis in ovarian carcinoma by targeting the nuclear factor-kappaB pathway, *Clin Cancer Res* 13, 3423-3430.
150. Savagner, P., Kusewitt, D. F., Carver, E. A., Magnino, F., Choi, C., Gridley, T., and Hudson, L. G. (2005) Developmental transcription factor slug is required for effective re-epithelialization by adult keratinocytes, *J Cell Physiol* 202, 858-866.
151. Symowicz, J., Adley, B. P., Woo, M. M., Auersperg, N., Hudson, L. G., and Stack, M. S. (2005) Cyclooxygenase-2 functions as a downstream mediator of lysophosphatidic acid to promote aggressive behavior in ovarian carcinoma cells, *Cancer Res* 65, 2234-2242.
152. Forget, P., Vandenhende, J., Berliere, M., Machiels, J. P., Nussbaum, B., Legrand, C., and De Kock, M. (2010) *Do intraoperative analgesics influence breast cancer recurrence after mastectomy? A retrospective analysis*, Anesth Analg 110, 1630-1635.

The invention claimed is:

1. A method of modulating GTPase in a human patient with ovarian cancer, the method comprising administering to said patient an effective amount of a composition consisting essentially of R-ketorolac as an enantiomerically pure individual optical isomer, or a pharmaceutically acceptable salt thereof.

2. The method according to claim 1 wherein said cancer is metastatic.

3. The method according to claim 1 wherein said cancer is recurrent.

4. A method of treating ovarian cancer in a human patient in need thereof comprising administering to said patient a composition consisting essentially of an effective amount of R-ketorolac as an enantiomerically pure individual optical isomer or pharmaceutically acceptable salts thereof, optionally in combination with carboplatin, cisplatin, docetaxel, paclitaxel or a mixture thereof.

5. The method according to claim 4 wherein said R-ketorolac is administered to said patient in combination with carboplatin, cisplastin, docetaxel, paclitaxel or a mixture thereof.

6. The method according to claim 4 wherein said cancer is metastatic cancer.

7. The method according to claim 4 wherein said cancer is recurrent cancer.

8. The method according to claim 5 wherein said cancer is metastatic cancer.

9. The method according to claim 5 wherein said cancer is recurrent cancer.

* * * * *